(12) United States Patent
Podoleanu et al.

(10) Patent No.: US 11,717,154 B2
(45) Date of Patent: Aug. 8, 2023

(54) IMAGING APPARATUS AND METHOD

(71) Applicant: University of Kent, Canterbury (GB)

(72) Inventors: Adrian Podoleanu, Canterbury (GB); Manuel Marques, Herne Bay (GB); Michael Hughes, Staplehurst (GB)

(73) Assignee: University of Kent, Canterbury (GB)

( * ) Notice: Subject to any disclaimer, the term of this patent is extended or adjusted under 35 U.S.C. 154(b) by 860 days.

(21) Appl. No.: 16/521,859

(22) Filed: Jul. 25, 2019

(65) Prior Publication Data

US 2020/0037871 A1 Feb. 6, 2020

(30) Foreign Application Priority Data

Jul. 26, 2018 (GB) ..................... 1812199

(51) Int. Cl.
*A61B 3/10* (2006.01)
*A61B 3/00* (2006.01)
*A61B 5/00* (2006.01)
*G01N 21/47* (2006.01)

(52) U.S. Cl.
CPC ............ *A61B 3/102* (2013.01); *A61B 3/0008* (2013.01); *A61B 5/0066* (2013.01); *G01N 21/4795* (2013.01)

(58) Field of Classification Search
CPC ...... A61B 3/0008; A61B 3/102; A61B 5/0066
See application file for complete search history.

(56) References Cited

U.S. PATENT DOCUMENTS

| | | | | |
|---|---|---|---|---|
| 3,864,044 A | * | 2/1975 | Lyshkow | G01N 21/255 250/573 |
| 4,767,171 A | * | 8/1988 | Keil | G02B 6/2937 385/35 |
| 8,451,452 B2 | * | 5/2013 | Podoleanu | G01B 9/0209 356/497 |
| 8,619,184 B2 | | 12/2013 | Podoleanu | |
| 9,167,144 B2 | | 10/2015 | Podoleanu | |
| 9,339,178 B2 | | 5/2016 | Yu et al. | |
| 9,383,187 B2 | | 7/2016 | Podoleanu et al. | |

(Continued)

OTHER PUBLICATIONS

Fechtig, et al., "Line-field parallel swept source MHzOCT for structural and functional retinal imaging", Biomedical Optics Express, vol. 6, No. 3, Mar. 1, 2015, pp. 716-735.

(Continued)

*Primary Examiner* — Violeta A Prieto
(74) *Attorney, Agent, or Firm* — Dinsmore & Shohl LLP

(57) ABSTRACT

The present disclosure relates to an apparatus and method that can be used to remotely acquire high resolution depth resolved images from a sample. The apparatus employs an adapter to an imaging device, where the adapter uses a minimum of components to produce interferometry patterns on the input facet of the imaging device. The imaging device can be a bundle endoscope terminated on a camera sensor or on several camera sensors or simply a camera sensor. In conjunction with a swept source or a broadband source, at least one camera sensor may be employed to provide optical coherence tomography (OCT) images of the sample. When the imaging device uses a bundle of optical fibers, the apparatus and method can provide OCT images tolerant to bending of the bundle.

20 Claims, 14 Drawing Sheets

(56) References Cited

U.S. PATENT DOCUMENTS

| | | | |
|---|---|---|---|
| 2011/0043661 A1* | 2/2011 | Podoleanu | G01B 9/0203 |
| | | | 348/370 |
| 2011/0134436 A1* | 6/2011 | Podoleanu | G01B 9/02004 |
| | | | 356/512 |
| 2011/0261367 A1 | 10/2011 | Gmitro et al. | |
| 2015/0185390 A1* | 7/2015 | Hu | G02B 19/0061 |
| | | | 362/558 |
| 2017/0138721 A1 | 5/2017 | Podoleanu et al. | |
| 2022/0171332 A1* | 6/2022 | Cuche | G02B 23/2492 |

OTHER PUBLICATIONS

Fechtig, et al., "Line-field parallel swept source interferometric imaging at up to 1 MHz", Optics Letters, vol. 39, No. 18, Sep. 15, 2014, pp. 5333-5336.

Yasuno, et al., "One-shot-phase-shifting Fourier domain optical coherence tomography by reference wavefront tilting", Optics Express, vol. 12, No. 25, Dec. 13, 2004, pp. 6184-6191.

Wang, et al., "Full-Field Swept Source Master-Slave Optical Coherence Tomography", IEEE Photonics Journal, vol. 7, No. 4., Aug. 2015, Art No. 3800114.

\* cited by examiner

Figure 1'A.

IMAGING APPARATUS AND METHOD

CROSS REFERENCE TO RELATED APPLICATIONS

The present specification claims the benefit of United Kingdom Patent Application No. GB 1812199.6 filed on 26 Jul. 2018 and entitled "Imaging Apparatus and Method," the entirety of which is incorporated by reference herein.

FIELD

The present specification relates to an apparatus and method that can be used to acquire depth resolved images from a sample, in particular, to an apparatus and method to remotely acquire high resolution depth resolved images.

BACKGROUND

Several scanning probes have been devised to perform scanning in confined spaces. A problem with such probes is that it is difficult to miniaturize a high speed, high resolution scanning system, and so probes tend to be slow, low resolution or large-diameter. It would be advantageous if the OCT method could instead be applied via imaging bundles, knowing that that they can provide micron-order lateral resolution by utilizing numerous fibers placed together. It would also be advantageous if the OCT method could be applied via Hopkins rods, as they also provide good lateral resolution.

Different reports using bundles for OCT exist. Scanning the proximal end represents a solution for endoscopy, as disclosed in the U.S. Pat. No. 9,339,178 B2, by L. Yu and K. Parto. To compensate for the bundle dispersion, another similar bundle is inserted in the reference arm of the interferometer. However, the fibers in the bundles present different lengths and therefore the optical path differences measured are corrupted by the length variation from one fiber in the bundle to next. Further, multimode behavior of the fiber cores leads to multiple ghost images.

Common path interferometry is possible using a reflective window at the end of the bundle, as disclosed in the USA patent application: 2011/0261367 A1, by A. F. Gmitro and H. Makhlouf. By using the common path, the variation in the length of fibers inside the bundle does not present a problem for the generation of a correct OCT image. However, if the sample to be investigated is at a distance, then sensitivity is low, because of the drop off of sensitivity with optical path difference (OPD), characteristic of spectral domain and Fourier domain OCT. For non-scanning systems using cameras at the proximal end, the internal reflections from the fiber ends and from the common path reflector limit sensitivity. For this reason, bundles are generally used with separate illumination in camera endoscopy.

Therefore, a need exists for employing bundles to perform depth resolved imaging via OCT. A need exists for devices that are simple, small volume, and exhibit tolerance to bundle bending. A need exists for a small diameter conduit while securing sufficient transversal resolution in the image. A need exists to use bundles with cameras in OCT. A need also exists to perform OCT imaging via Hopkins rods.

SUMMARY

An apparatus for imaging a sample is disclosed, according to claim 1.

The apparatus employs an adapter between the sample and an imaging device, where the adapter may include a minimum of components to produce interferometry patterns on the input facet of the imaging device. The routing of beams inside the adapter and illumination of the sample are such that the adapter facilitates miniaturization, making the apparatus useful in acquiring depth resolved images from confined spaces such as lung, the gastrointestinal tract or the internal structure of the eye. The imaging device can use an optical relay device to convey the interference pattern created by the adapter to a camera sensor or can transfer the interference pattern directly to a camera sensor. In conjunction with a swept source or a broadband source, at least one camera sensor may be employed to provide optical coherence tomography (OCT) images of the sample. When the imaging device uses a bundle of optical fibers, the apparatus and method provide OCT images tolerant to bending of the bundle.

The apparatus may be used for remote imaging, meaning that the imaging device is spaced from the sample to be imaged, and an optical path between the sample and the imaging device may include an optical relay device.

Light may be sent to the sample either directly from the first output of the first splitter, or through at least a part of the interface optics, and/or through another optical component such as an optical fiber.

The imaging device may be illuminated with the divergent reference light either directly from the first reference fiber, or through parts of the interface optics, and/or through another optical component.

An end of the first reference fiber may be oriented towards the imaging device.

According to embodiments, the scattered light returns from the sample without passing through the first splitter.

The first splitter may be a one-by-two fiber splitter.

The first output of the first splitter and the second output of the first splitter may be placed symmetrically, at opposing sides of the optical axis of the interface optics.

In a first aspect, an imaging system is disclosed that uses an adapter applied to an imaging device to perform OCT. To this goal, the adapter uses a first feeding fiber to a first splitter to produce two beams, a first sample beam that is projected onto the sample under investigation and a first reference beam that is projected onto the imaging device. By using interface optics between the sample and the imaging device, with the sample and imaging device at conjugate points in respect to the interface optics, superposition of rays back-scattered from the sample is performed with the rays from the reference beam, producing an interference pattern on the imaging device. Divergent illumination of each of the sample and of the imaging device minimizes the number of components in the interface optics and adapter and allows miniaturization. The imaging device may consist of a camera device or of an optical relay device (ORD) terminated on a camera device, in which case the adapter can be used to transform a microendoscopy imaging system into an OCT system where the ORD can be a fiber bundle, a telescope, a GRIN rod, a taper or a Hopkins rod.

In a second aspect, the adapter comprises a second feeding fiber to a second splitter whose fiber outputs are placed symmetrically in relation to an optic axis of the interface optics, to the outputs of the first splitter. This allows illumination of the sample from two different angles opening the possibility of pseudo stereo imaging, angular scattering imaging or polarization enhancement or polarization imaging.

In a third aspect, a system is disclosed that includes the second feeding fiber employed to image the sample either directly or via the second splitter for a non OCT type of imaging, such as fluorescence or Raman for enhanced functionality.

In a fourth aspect, when the ORD uses a fiber bundle, the fiber (or fibers) feeding the adapter is (are) one of the fibers in the bundle. It is also possible for the sample fiber and reference fiber to be run along the fiber bundle or use fibers in the fiber bundle to serve as sample and reference fibers.

In a fifth aspect, a prism or prisms, a half ball lens or half ball lenses are used at the end of fibers to deflect divergent rays at a large angle from the fiber axis.

In a sixth aspect, the fibers are terminated with ball lenses to increase the divergence of rays coming out of the fibers, to widen the area covered by diverging rays.

In a seventh aspect, a hole or holes in lenses in the interface optics are used to allow miniaturization and control of angle between the interfering rays.

In an eighth aspect, the interface optics in the adapter is combined with the optics of the eye to project images of the retina on the imaging device to achieve OCT imaging of the retina in the eye.

In a ninth aspect, the adapter is miniaturized to fit a rigid endoscope or a Hopkins rod as part of the imaging device, for general surgery or medical robotics, or to fit a rigid miniature borescope for vitreous retinal surgery of the eye.

In a tenth aspect, a system is disclosed using a fiber bundle as the ORD part of the imaging device, where the proximal end of the bundle is interfaced to a smart phone or commercial digital camera.

In an eleventh aspect, the camera device comprises a dichroic splitter and two camera sensors for simultaneous microendoscopy and OCT imaging.

In a twelfth aspect, a remote imaging system is disclosed that can be assembled inside a lightweight, hand-held, totally passive ophthalmic OCT probe allowing non-standard patient imaging sessions (e.g. with the patient in supine position).

In a thirteenth aspect a method for remote imaging of a sample is disclosed that employs an interference pattern of backscattered light returned by sample with reference light, interference pattern that takes place at the input of an imaging device, where the sample is illuminated by diverging light from one output of a two-output splitter and the reference light is obtained by diverging light from the other output of the splitter, and where the splitter is driven by an optical source.

In a fourteenth aspect a method to recover depth resolved information from the sample includes using a swept source as the optical source and by using complex master slave interferometry to process signal collected by each pixel of a camera sensor capturing multiple frames of the interference pattern while sweeping the optical frequency of the optical source.

In a fifteenth aspect a method to produce a cross section OCT image from the sample includes using a broadband source as the optical source and by projecting a line selected from the interference pattern via a dispersing element on a 2D camera sensor to capture the spectral dimension of the line along a spectral direction perpendicular to the direction of the line selected from the interference pattern, and by using complex master slave interferometry applied to the row of pixels in the camera sensor along the spectral direction.

In a sixteenth aspect, a method is disclosed that can serve polarization imaging tolerance, or polarization sensitive imaging, or angular investigation, sequential or simultaneous endomicroscopy with OCT, where either or both regimes of operation may perform spectroscopic analysis.

BRIEF DESCRIPTION OF THE DRAWINGS

The novel features which are believed to be characteristic of the present embodiments, as to their structure, organization, use and method of operation, together with further objectives and advantages thereof, will be better understood from the following drawings in which embodiments will be illustrated by way of example. It is expressly understood, however, that the drawings are for the purpose of illustration and description only and are not intended as a definition of the limits of the embodiments described herein. Various embodiments will now be described in association with the accompanying drawings in which:

FIG. 1' shows a schematic diagram of yet another version of an embodiment of the adapter for performing optical coherence tomography.

FIG. 1'A shows a schematic diagram of another version of the adapter in FIG. 1' to perform optical coherence tomography.

FIG. 2' shows a more detailed version of the first embodiment of the adapter, in FIG. 1' and FIG. 1'A.

FIG. 2" shows a variation of the first embodiment of the adapter.

FIG. 15' shows a version of the embodiment in FIG. 15 adapted to low resource settings.

FIG. 23' shows a section through the optical relay device implemented as a bundle, where the two feeding fibers are part of the bundle assembly, FIG. 23" shows a section through the optical relay device implemented as a bundle, where the two fibers part of the interferometer are run along and within the bundle.

DETAILED DESCRIPTION

Figure 1:
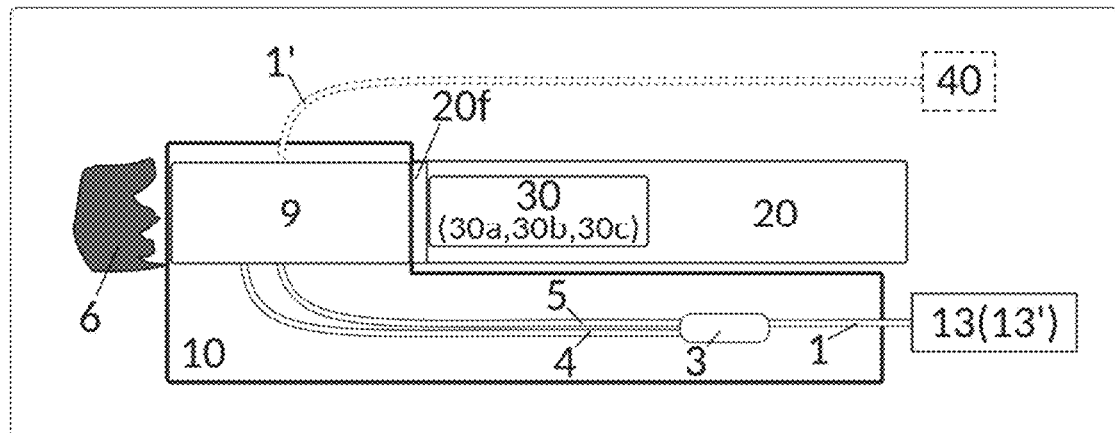
FIG. 1 shows a schematic diagram of a first embodiment of the adapter for performing optical coherence tomography.
Figure 1:
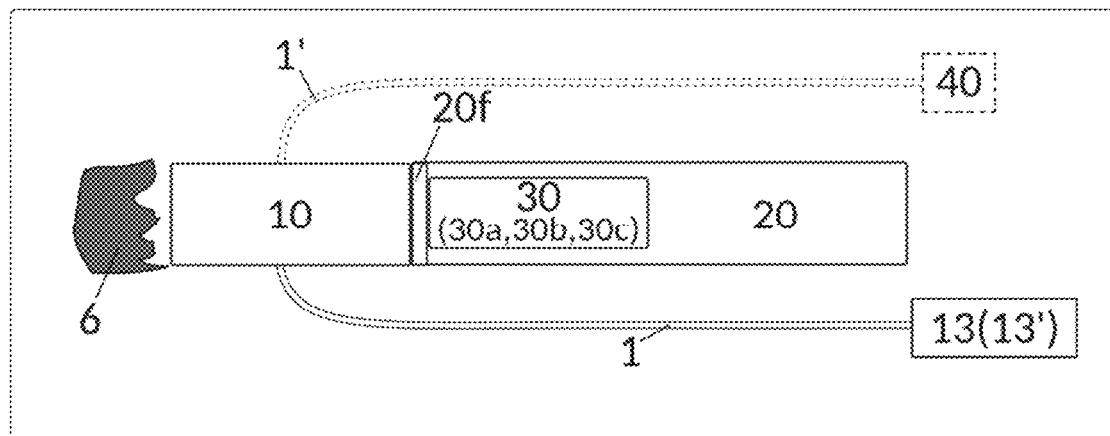

Various features of the apparatuses and methods, as well as other objects and advantages attendant thereto, are set forth in the following description and the accompanying drawings in which like reference numerals depict like elements.

FIG. 1 shows a first embodiment of a system for remote depth resolved imaging of a sample 6, comprising an adapter 10 and an imaging device 20, where the adapter comprises a splitter 3 fed by a first feeding fiber 1, connected to an optical source, that can be either a swept source 13 (ie a tunable laser of a sufficiently narrow linewidth), or a broadband source 13'. The splitter 3 delivers light into two output fibers, a sample fiber 4 and a reference fiber 5, where the two fibers feed light into an enclosure 9 placed between the sample to be investigated, 6 and the facet 20f of the imaging device 20, where the enclosure 9 accomplishes the following 4 functions: (i) projecting divergent light from the sample fiber 4 onto the sample 6, (ii) projecting light backscattered by the sample 6 on the facet 20f, (iii) projecting divergent light from the reference fiber 5 on the imaging device 20 and (iv) producing an interference pattern on the facet 20f, a pattern created between the divergent reference light with the light backscattered by the sample 6. The imaging device 20 comprises a camera device 30 that may contain one or more camera sensors. Variations of such camera device are shown in subsequent embodiments, as 30a, 30b and 30c. Additionally, some subsequent detailed embodiments comprise a second feeding fiber 1' driven by an extra optical source 40.

Figure 1A:
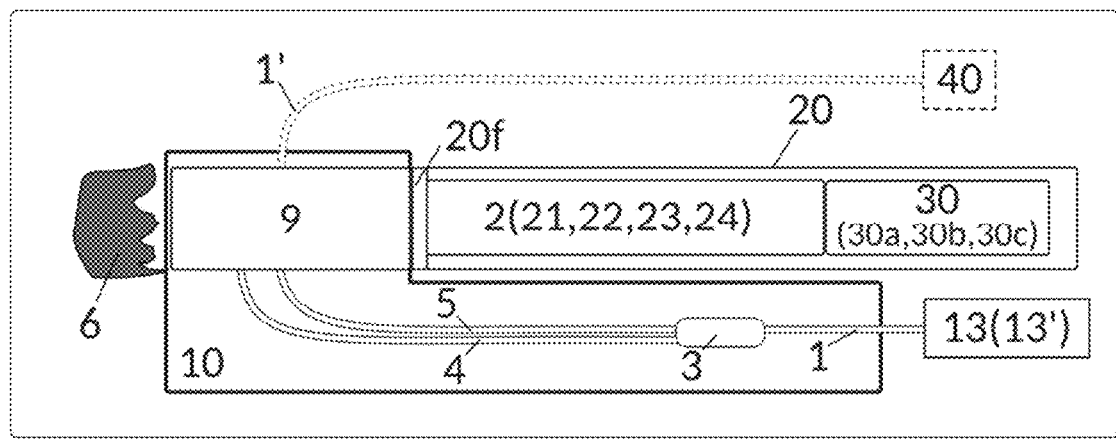
FIG. 1A shows a schematic diagram of another version of the embodiment of the adapter in FIG. 1 to perform optical coherence tomography.

FIG. 1A shows a version of the adapter 10 in FIG. 1, where the imaging device 20 comprises an optical relay device 2 with a distal end close to the enclosure 9 and its proximal end on the camera device 30. The optical relay device 2 can be a fiber bundle, 21, a GRIN rod or a lens 22, or a telescope or Hopkins rod 23, or a taper 24, or a combination of any two or more of such components.

In FIG. 1 and FIG. 1A, the two fibers 4 and 5 come along the imaging device 20. The facet 20f of the imaging device 20 is either the facet of the camera device 30 in FIG. 1 or the facet of the optical relay device 2 in FIG. 1A, ie its distal end. Ideally, in FIG. 1A, the optical relay device should relay the interference pattern from 20f onto the surface of the camera device 30.

FIG. 1' shows another version of the adapter 10 in FIG. 1, where the splitter 3 is placed inside the enclosure 9, allowing the structure of the adapter to be collapsed between the sample 6 and imaging device 20.

FIG. 1'A shows a version of the adapter 10 in FIG. 1A, where the splitter 3 is placed inside the enclosure 9, allowing the structure of the adapter to be collapsed between the sample 6 and imaging device 20.

In FIG. 1' and FIG. 1'A, the feeding fiber 1 and the additional feeding fiber 1' come along the imaging device 20 and the fibers 4 and 5 have short lengths.

Figure 2:
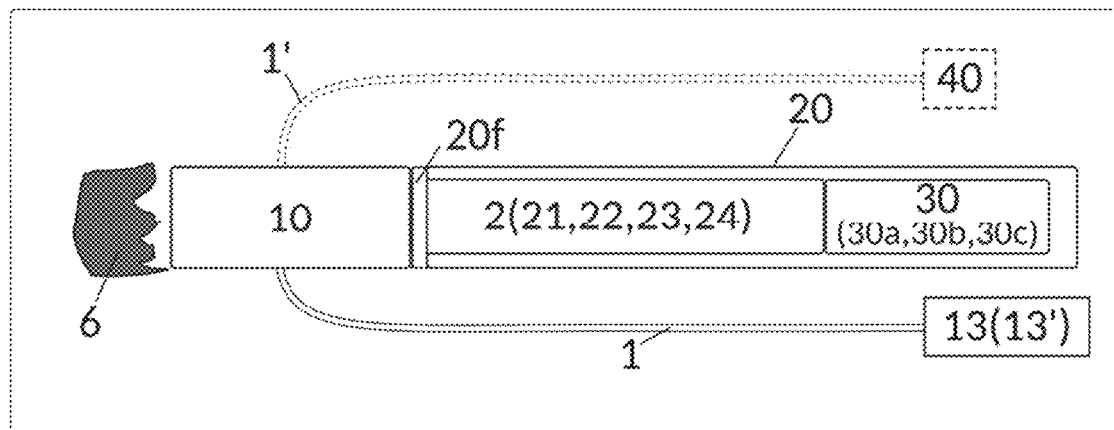
FIG. 2 shows a more detailed version of the first embodiment of the adapter, in FIG. 1 and FIG. 1A.
Figure 2:
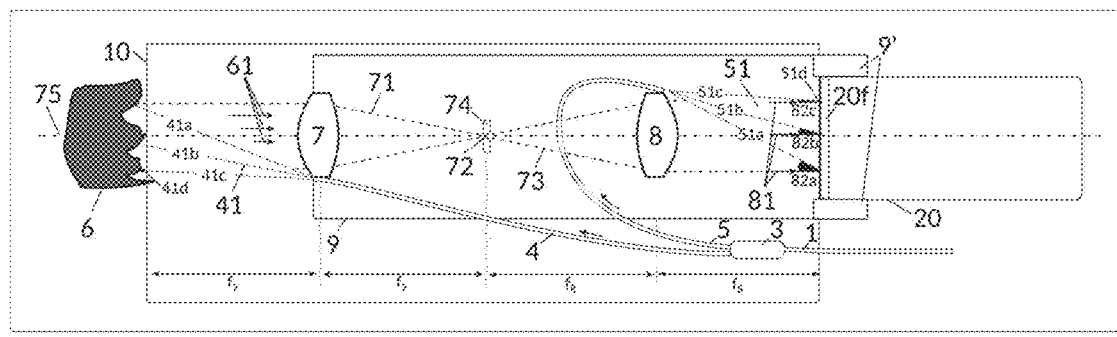
Figure 2:
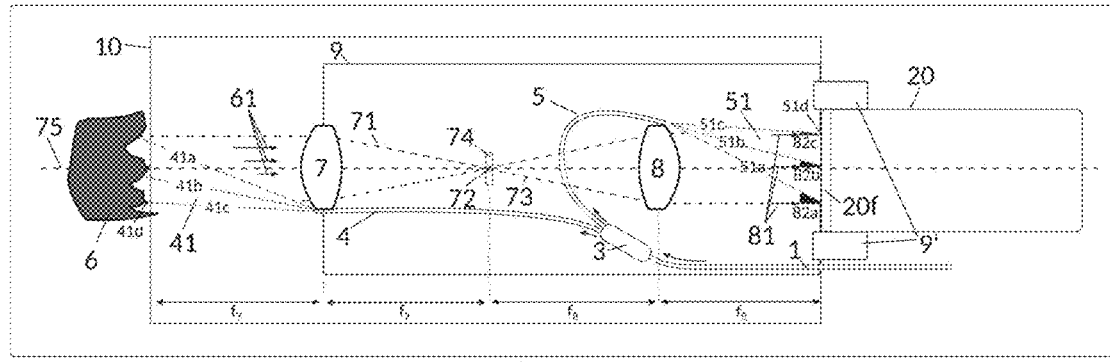
Figure 2:
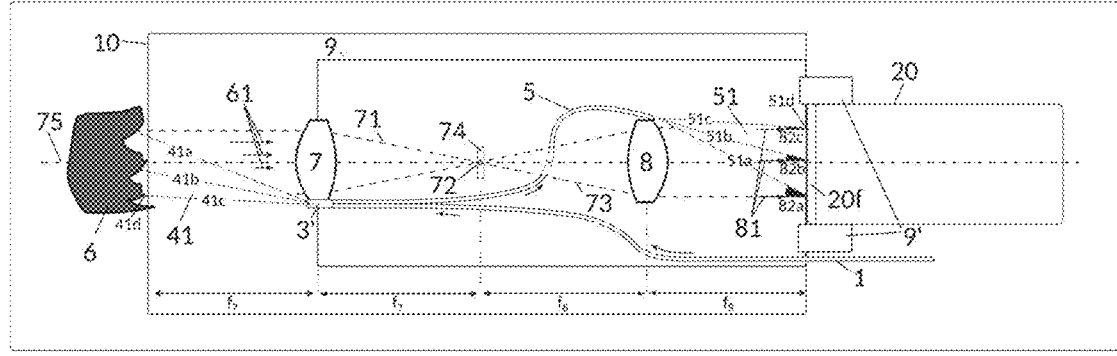

FIG. 2 shows in more detail the optics inside the adapter 10 in the embodiments in FIGS. 1 and 1A, organized as an interferometer and as an interface optics as explained below. Here the fiber splitter 3 is left outside the enclosure 9, where it is attached to the enclosure 9 to avoid obturation of light inside the enclosure 9. The splitter 3, whilst still part of the adapter 10, can also be placed closed to the proximal end of the imaging device 2, in which case fibers 4 and 5 are positioned along the imaging device 2, as illustrated in FIG. 1 and FIG. 1A. Light from sample fiber 4 diverges along rays 41, where three rays are shown only, 41a,b,c, to illuminate the sample to be investigated 6. The facet of the adapter, 10f, may be anti-reflection coated. The enclosure comprises an interface optics, made in this example of two lenses 7 and 8 in a telescope arrangement. Backscattered light from the sample 6 returns as rays 61 through the lens 7 that focuses the beam 71 of backscattered rays from the sample 6, behind lens 7 in a point 72, therefrom propagating via diverging rays 73 to lens 8, that focuses rays 81 behind it on the facet 20f of the imaging device 20. The interface optics relays an image of the sample 6 on the facet 20f, ie the top of the sample 6 and the facet 20f are conjugate points for the interface optics. An imaginary optic axis of the adapter can be considered as a line through the centers of lenses 7 and 8, point 72 and falling perpendicular to the facet 20f. Rays 81 from sample 6 propagate almost parallel to the optical axis 75 and perpendicular to the facet 20f. For the operation as a telescope, the distance between lenses 7 and 8 is the sum of focal length $f_7$ and $f_8$ of their respective focal lengths, where the sample 6 is essentially at $f_7$ and the facet 20f at $f_8$ from lens 8, according to principles known in the art. For further spatial filtration, a pinhole or aperture 74 is used. Rays 51 from reference fiber 5 diverge towards the facet 20f, only three rays are shown 51a,b,c, where they are superposed with rays 81 from the sample 6. In this way, interference is achieved with a minimum of elements, by using off axis illumination and divergent light that allows superposition of light rays from the sample with the reference rays without using any splitter and without any stray reflections. The superposition of sample rays 81 and reference rays 51 on the facet 20f of the imaging device 20 creates an interference pattern. Therefore, in case the optical relay device 2 is a fiber bundle 21, interference is not affected by bending it, as both rays 81 and 51 are disturbed similarly. By using a feeding fiber 1 with a splitter 3 and a minimum of optical elements in the enclosure 9, the adapter 10 can be assembled within a small size. The simplicity of the adapter is crucial for its miniaturization to be used in microendoscopy.

The enclosure 9 may be in the form of a cylindrical shape, sealed around lenses 7 and 8 in which case there is no facet 10f, no window.

A fixture 9' connects the enclosure 9 to the imaging device 20, which incorporates either the camera device 30 as shown in FIG. 1 or an optical relay device 2 as shown in FIG. 1A. The fixture 9' can be a nut, a clip or any other means that allow an easy attachment to the imaging device 20, or can be devised as a permanent solution, attached to either camera device 30 or to optical relay device 2.

In the practice of fiber devices, a fiber splitter (directional coupler), 3, is normally produced by fusing two fibers together and protecting the assembly of the two fibers for enhanced mechanical strength with a sheath or a tubing. Here, to satisfy the small size required, the fiber splitter can be reduced to the diameter of two single mode fibers, of less than 0.25 mm, Because the ratio in the optical power split needed is small, with a very low power of 1-5% or even smaller power redirected towards reference fiber, 5, a short interaction length is sufficient, that facilitates the assembly of a miniature splitter.

For enhanced mechanical strength, the fiber splitter 3 can be attached to the imaging device 20, or to the side of the optical relay device, 2, close to its distal end to reduce the lengths of the two fibers 4 and 5. Here, the splitter 3 is still shown as a fiber splitter, with short fibers 4 and 5 but other modalities are possible, compatible with the size of the adapter, such as using a miniature bulk beam-splitter.

FIG. 2' shows in more detail the optics inside the adapter 10 in the embodiments in FIG. 1' and 1'A, organized as an interferometer and as an interface optics as in FIG. 2, with the difference from FIG. 2 that the adapter is collapsed around the enclosure 9 and the splitter 3 is incorporated close to the lateral size of the enclosure 9 or placed inside the enclosure as shown. In comparison with the embodiment in FIG. 2, the fiber 4 and 5 are extremely short and less interference instabilities are produced.

The basic construction of the adapter as per embodiment in FIG. 2' allows a simple adaptation to existing bundle endoscopic systems by simply routing a single mode fiber as a first feeding fiber 1 to feed light to the adapter 10 and relaying the interference pattern via the bundle 21.

FIG. 2" shows another version of a splitter, 3', where the reference beam is created by reflection produced by the end of the fiber 1, acting also as fiber 4. A non-coated fiber end can return up to 4% from the light inside the fiber towards reference fiber 5. Fiber 5 and the end of fiber 1 are placed inside the enclosure 9.

Figure 3:
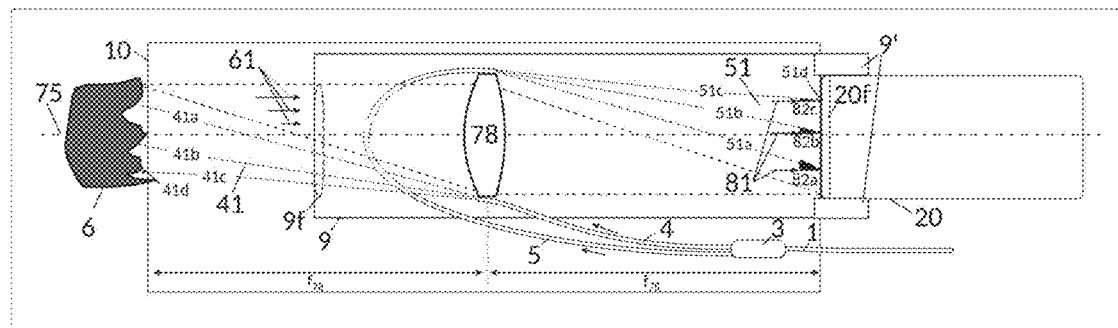
FIG. 3 shows yet another variation of the first embodiment of the adapter.

FIG. 3 shows another version of the interface optics inside the enclosure 9, consisting in a single lens, 78, of focal length $f_{78}$, that produces an image of the sample 6 on facet 20f in a configuration $2f_{78}$, $2f_{78}$. This simplifies the adapter structure, whilst the larger distance to sample 6 and to facet 20f from fiber ends allows a larger area covered on the sample 6 and facet 20f of the respective divergent cones of rays 41 and 51, than in FIG. 2, 2', 2".

In all embodiments in FIG. 2, 2', 2" and 3, there is an angle between the two interfering rays, 82, that is medium in the center, 82b, varying to a larger value for the ray 51a, to 82a, and varying to a smaller value for the ray 51c, to 82c. A non-zero angle defines the interference process as off-axis, where the larger the angle, less the interference strength. In addition, the interference strength becomes slightly dependent on polarization as detailed more below. However, direct delivery of light to the sample 6 and to the place of their superposition, facet 20f, is key in avoiding the use of a splitter in the path of light to and from the sample 6, enabling a structure of the adapter that can be miniaturized.

To secure similar path lengths in the diverging rays of the sample and reference waves, the two fibers, 4 and 5 are placed oppositely within the adapter, in respect to the optic axis 75. The ray 41a travels longer than the ray 41c. The same is true for the ray 51a that travels longer than the ray 51c.

Figure 4:
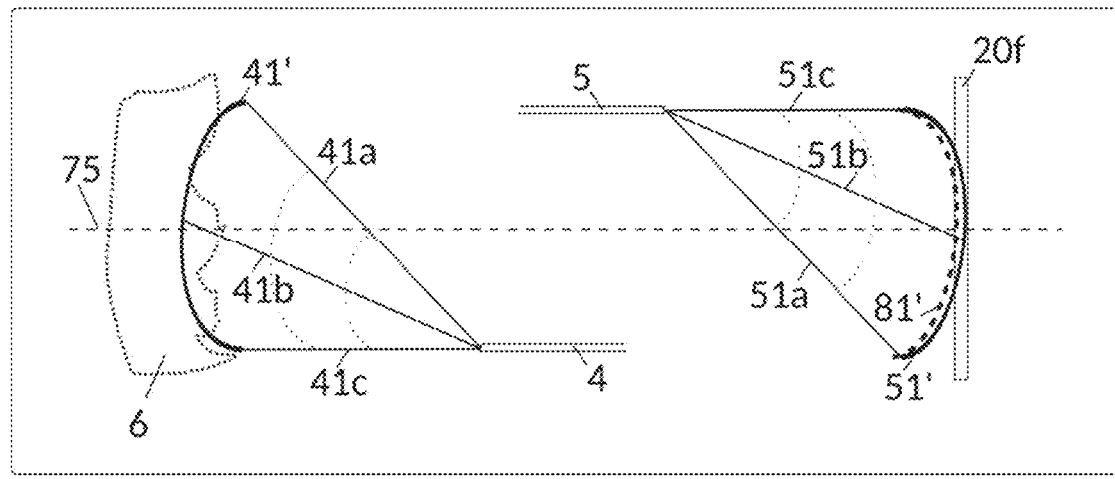
FIG. 4 explains the principle of matching the locus of equal optical path length in the reference beam with the locus of equal path length in the sample beam under off axis and divergent illumination.

The matching of curvature of optical path loci for the two interfering sets of rays (waves or beams) is better understood using the sketch in FIG. 4. Let us consider the path length of rays 41 as the radius of a sphere, 41', with the origin on the tip of fiber 4. Similarly, the locus 51' is spherical for the path lengths of rays 51. Via the interface optics (lenses 7 and 8 in FIG. 2, 2' and 2" and lens 78 in FIG. 3), the locus 41' is optically conjugate to the locus 51'. If the two locuses are perfectly matched, then the fringe pattern on facet 20f is uniform, otherwise, slight mismatches introduce a periodicity of fringes, similar to Fizeau fringes and larger mismatches would make the finge pattern exhibit nonuniform periodicity.

The optical path difference (OPD) in the interferometer in FIGS. 2 and 2' so implemented is:

$$\text{OPD} = (n \text{ length of fiber} + \text{length of rays } 41 + \text{length of rays } 61 + n \text{ thickness lens } 7 + \text{length of rays } 71 + \text{length of rays } 73 + n \text{ thickness lens } 8 + \text{length of rays } 81) - (n \text{ length of fiber } 5 + \text{length of rays } 51) \quad (1)$$

where n is the index of refraction of the fibers. In these equations the index of refraction for lenses 7 and 8 was considered similar, n, with that of the fibers 4 and 5. While the length of rays 41 is similar to the length of rays 51, the OPD equation shows that for OPD=0 the length of fiber 5 needs to be longer than the length of fiber 4 to compensate for the longer air path of the sample rays along rays 41, 71 and 73 and along the lenses 7 and 8. Therefore some dispersion is inherent to this assembly.

For OPD=0, length of rays 41+length of rays 61+length of rays 71+length of rays 73+length of rays 81−length of ray 51+$n$ (thickness lens 7+thickness lens 8)=$n$ (length of fiber 5−length of fiber 4). (2)

For the splitter in FIG. 2", the equations above are still valid with the length of fiber 4 equal to zero.

For the interface optics in FIG. 3,

OPD=($n$ length of fiber 4+length of rays 41+length of rays 61+$n$ thickness lens 78+length of rays 81)−($n$ length of fiber 5+length of rays 51) (3)

where n is the index of refraction of the fibers.

For OPD=0, length of rays 41+length of rays 61+length of rays 81+$n$ thickness lens 78−length of ray 51)=$n$ (length of fiber 5−length of fiber 4). (4)

Miniaturizing the Adapter

Figure 5A:
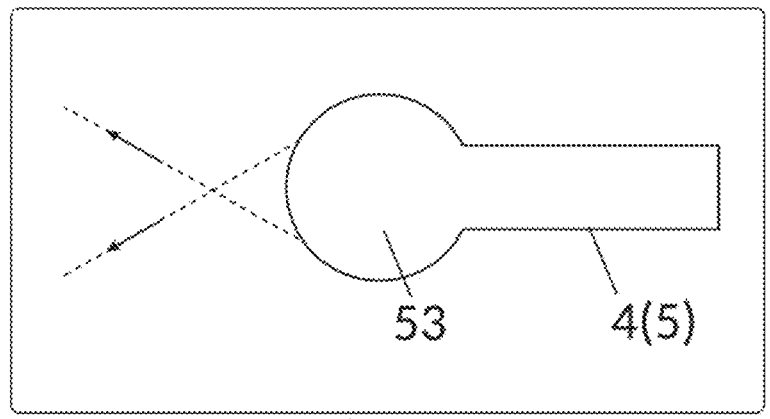
FIG. 5A shows ball lenses to be used on ends of fibers to increase the divergence of rays and create a larger illuminated area than that with the fibers alone.

Single mode fibers present a numerical aperture of ~0.1. Simple projection of rays is used in the embodiments in FIG. 2, 2' and 2". However, if the distance to sample 6 from fiber 4 is reduced, as well as the distance from fiber 5 to facet 20$f$, the illuminated areas by each such fiber on 6 and respectively on 20$f$ may be too small. Therefore, the fiber ends may be terminated with ball lenses 53 as shown in FIG. 5A. Such ball lenses are known in the art, and employed in coupling light from semiconductor devices. They present sub-millimeter focal lengths, that can be advantageously used here to create a large diverging cone after the initial point of their focus. With a single-mode optical fiber, the spot size at roughly 1 mm in front of the fiber end is less than 200 microns, which is too small; with a ball lensed fiber at the same distance this figure is more than trebled, to 700 microns. With such ball lensed fibers, it is possible to create a spot size of more than 1 mm in diameter at a distance of over 2-3 mm. Aiming for a millimeter-sized illuminated area on the sample 6 and facet 20$f$, sub-millimeter size ball lenses can be used.

Figure 5B:
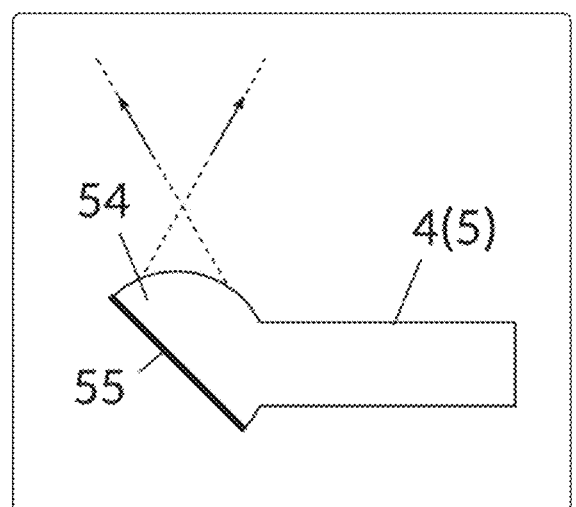
FIG. 5B shows a half-ball lens for deflection of the beam at a large angle from the fiber axis, to be used at the end of fibers.

For redirection of rays from fibers 4 in FIGS. 2 and 2' and from fiber 5 in FIG. 2, 2' and 2", the fiber ends can be terminated with half balls 54 as shown in FIG. 5B, where the total reflection at surface 55 rotates the beam by 90 degrees. These devices may be advantageously used in the embodiments described herein, to redirect the rays and help with the bending of fibers in the confined space of the adapter 10, especially when the enclosure 9 is reduced in size. A ball 53 or a half-ball 54 can also be used on the end of fiber 1 in FIG. 2", making sure that sufficient power is returned from the curved surface of the ball towards fiber 5.

Figure 5C:
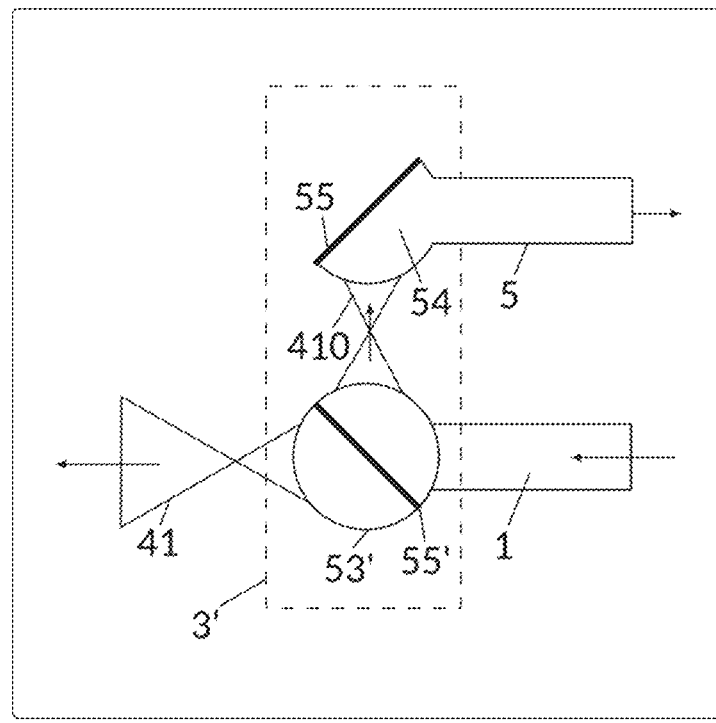
FIG. 5C shows an embodiment of a fiber miniature splitter.

FIG. 5C shows a splitter 3' to be used in a miniaturized version of the adapter 10. Here light from feeding Fiber 1 is terminated with a lens 53' that directs a beam of rays ahead as 41 and a beam of rays 410 reflected laterally by a thin splitter inside, 55', towards the half ball 54. The ball lens 53' is made from two half balls 54 with a coating in between of a different index of refraction than the material of balls to reflect a few percentages of light necessary to create the reference beam injected into the fiber 5. It may be possible that the two balls 53' and 54 are close to each other and touching in which case the path of rays 410 is very short.

Adapters with Reduced Angle of Rays with the Enclosure Axis

By miniaturizing the adapter, the angle 82 between the object rays 81 and reference rays 51 may increase to that extent that the consequent increase in the density of the fringe pattern over the facet 20$f$ cannot be properly sampled by the imaging device 20. For instance, by reducing the length of the enclosure 9, while keeping the same diameter, the angle between the two sets of rays increases. Any optical relay device 2 and camera device 30 reading the interference pattern have a limit in terms of fringe density that can be correctly sampled. Therefore, control of the angle is necessary.

For similar divergence of rays 41 on sample 6 with divergence of rays 51 on facet 20$f$, there should not be any OPD variation in the section of 20 on facet 20$f$ (in the drawing plane), so the fringe pattern should exhibit no cycles or only a small number of cycles due to mismatch between the curvature of the object wavefront 41' from 41 and the curvature of the reference wavefront 51' from 51, as illustrated in FIG. 4. However, the smaller the size of the adapter, the larger the difference between the angle of rays 41 with the enclosure axis and the angle of reference rays 51 with the enclosure axis, so the denser the fringe pattern over the facet 20$f$. Therefore, the fringe pattern may not be sampled properly by the camera or cameras in camera device 30 due to a combination of the limitations mentioned above.

Figure 6:
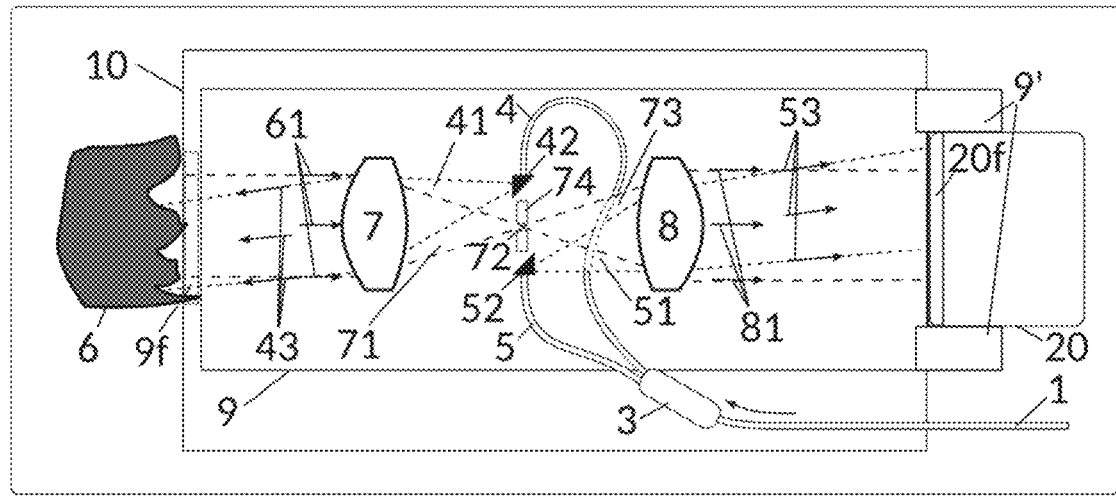
FIG. 6 discloses, in diagrammatic form, another embodiment of the adapter where the fiber ends are terminated with prisms placed off-axis between the lenses.

To minimize the angle, especially important when the enclosure 9 is reduced in length, or miniaturized, the embodiment shown in FIG. 6 uses placement of end of fibers 4 and 5 closer to the enclosure axis, where light rays from fibers 4 and 5 now employ the respective lenses 7 and 8. To deflect light from the fiber 4 a tiny prism 42, or a half ball 54 as shown in FIG. 5B can be used at the end of fiber 4. The diverging sample beam 41 becomes 43 after lens 7. The prism 42 (or half ball 54) and launching point of the sample beam is placed close to the focus point 72, but sufficiently away from 72 to avoid intercepting the rays 71 returned by sample 6, as little as possible. Placement of prism 42 closer to lens 7 will diverge beam 43 more behind lens 7, advantageous in covering a larger area of sample 6. The same strategy in reducing the obscuration of rays is valid for reference fiber 5, where its prism 52 (or a half ball lens 54), should be placed close to but sufficiently away from focus 72, producing the beam 51 diverging towards lens 8 and beam 53 behind lens 8. Spherical curvature of path variation due to the tip of fiber 4 being placed closer than $f_7$ to lens 7 can be compensated by placing the tip of fiber 5 closer than $f_8$ to lens 8. In this way, the OPD variation across facet 20$f$ is minimized. The interfering waves are now those of rays 81 and 53.

Figure 7:
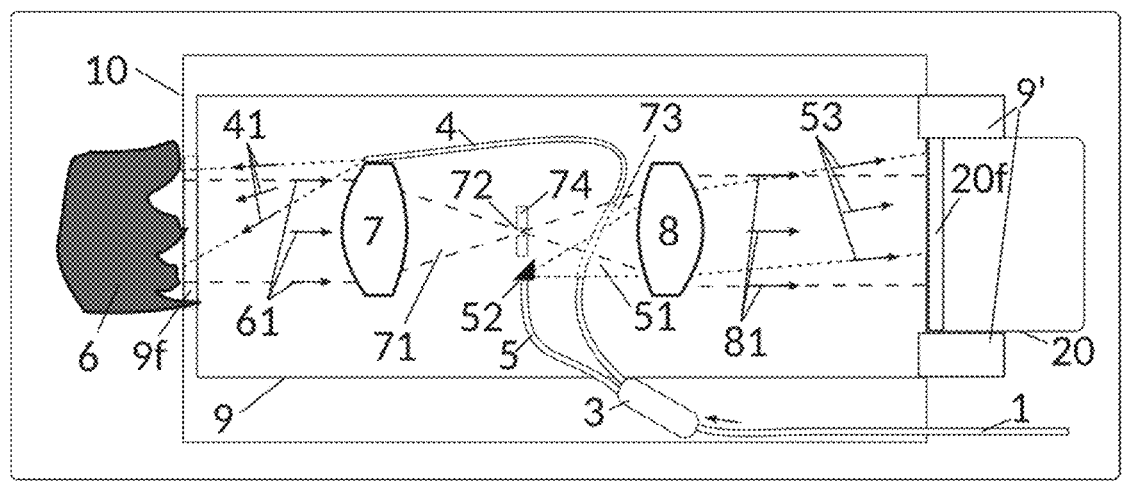
FIG. 7 discloses a variation of the embodiment in FIG. 6, where only the reference fiber is placed between the lenses and uses a prism.

In the embodiment in FIG. 7, the reference fiber 5 terminated with a prism 52 (or half ball 54) is placed between the lenses 7 and 8 only, while the sample fiber 4 can retain the same placement as in the previous embodiment in FIG. 2 and FIG. 2'. The rays 81 come on axis, but in terms of path difference there is a spherical variation imprinted by the off axis placement of the tip of fiber 4. This leads to an angular variation of path in the sample rays 41 not compensated in the reference rays 53. In the embodiment in FIG. 2 and FIG. 2' this was matched by the curvature of path locus of reference rays 51. Here, the curvature imprinted by diverging rays 41 cannot be compensated, as rays 53 although off-axis, are almost collimated. This will lead to a variation of periodicity of the fringe pattern within the facet 20$f$. This variation of periodicity can be however partially reduced by moving the end of fiber 5 closer to lens 8. This will increase the divergence of rays behind lens 8, however a perfect match in OPD for all rays 53 in OPD with rays 41 may not be possible. Alternatively, a given periodicity in transversal section 20f of the fringe pattern will correspond to a non-planar section in the sample 6, deviating away from a plane perpendicular on the optical axis of the adapter. This will only affect the interpretation of image and not its quality.

To avoid reflections from lens 7, lens 7 in FIG. 6 needs to be anti-reflection coated.

If the area covered by diverging rays from fiber 4 on sample 6 is not sufficiently large, then a ball lens 53 as shown in FIG. 5A can be added to the fiber end.

Figure 8:
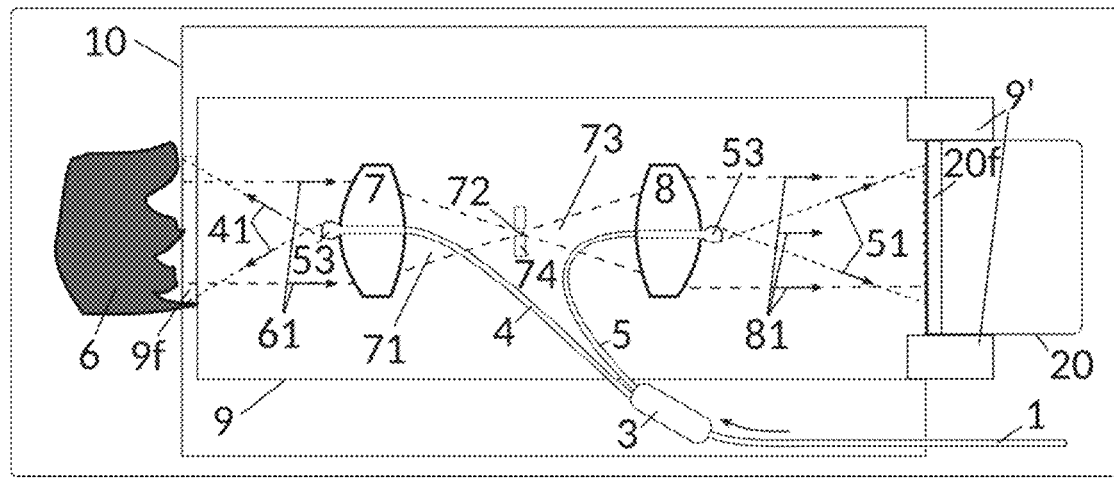
FIG. 8 shows, in diagrammatic form, another embodiment of the adapter where light from each fiber is routed through holes in the telescope lenses, to avoid light being intercepted by the lenses.

The embodiment of the adapter in FIG. 8 uses a hole in the lens 7 to send light from fiber 4 towards the sample 6, that eliminates the reflections from lens 7 in the embodiment in FIG. 6. The reference fiber 5 can be still left off axis as shown in the previous embodiment in FIG. 2 and FIG. 2', or be placed similarly, through a hole in lens 8, as shown in FIG. 8, in which case the path locus 41' of rays 41 and path locus 51' of rays 51 is similar, although the full field illumination of sample 6 and facet 20f is divergent and most of the rays are off-axis. To cover a sufficient area, the fiber ends may be equipped with spheres 53 as shown, however if $f_7$ and $f_8$ are sufficiently large, the spheres may not be necessary. If $f_7=f_8$, then the curvature of the path locus 41' and path locus 51' coincide.

Figure 9:
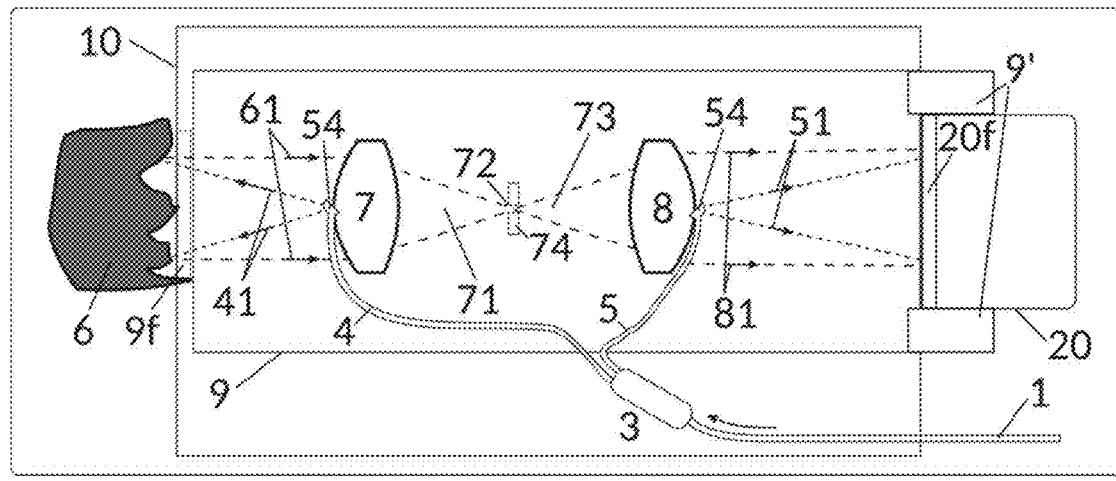
FIG. 9 represents a variation of the embodiment in FIG. 8, where the fibers are placed, one in between the sample and first lens and the second between the second lens and the facet of the optical relay device.

As disclosed in FIG. 9, another embodiment of the adapter uses the fibers 4 and 5 very close to respective lenses 7 and 8, using half spheres 54. No holes are necessary in the lenses 7 and 8, with the disadvantage of some shadows due to the fibers obscuring rays 61 and 81.

The embodiments disclosed in FIGS. 8 and 9 have shown the ends of fibers 4 and 5 placed at the center of lenses 7 and 8, but off-center placement of the fiber ends is also possible in these embodiments.

It should be evident, that by adding conditioning optics elements such as balls 53, half balls 54 or prisms 42 and 54 to the fiber tips of fibers 4 and 5, as long as these elements are identical, the optical path difference in the interferometer of the adapter 10 is not affected.

Retina Imaging

Figure 10:
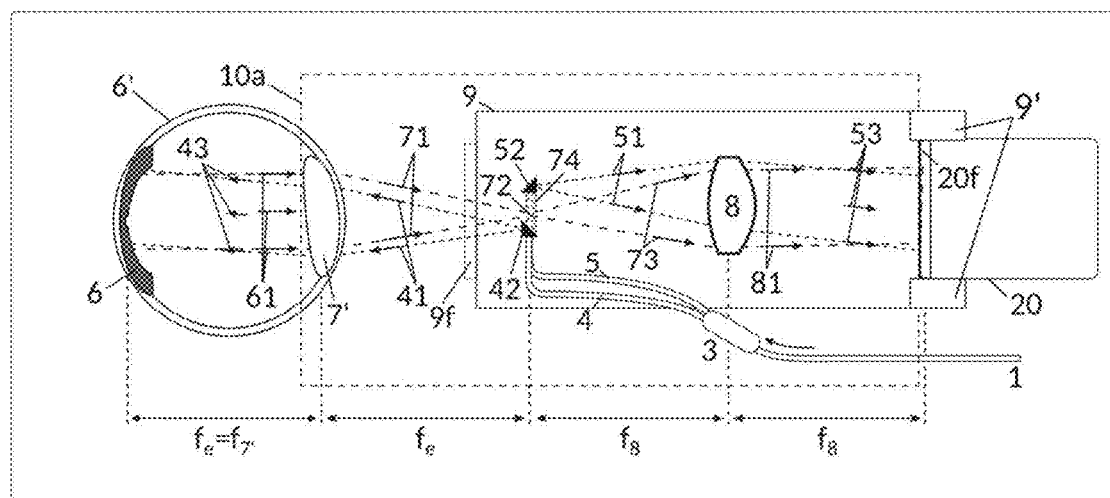
FIG. 10 shows a variation of the embodiment of the adapter in FIG. 6, to image the retina in an eye.

An embodiment of an adapter 10a, to image the retina 6 behind the eye lens 7' of an eye 6', is shown in FIG. 10. Here the lens 7 used in the adapter 10 is replaced by the eye lens 7'. The area covered on the retina is that similar to the area covered by the cone of diverging rays 41 on the cornea, if the launcher, fiber tip of fiber 4 or prism 42 is placed at a distance similar to the focal length of eye lens 7', $f_e$ as shown in the FIG. 10, which is not the case to be implemented in practice as detailed below. The telescope arrangement is now between lens 7' and lens 8, where an image from the retina 6 is projected on the facet 20f, i.e. retina 6 and facet 20f are at conjugate points in respect to telescope of lenses 7' and 8. Due to the shift of the launching prism 42 away from point 72 (as shown in FIG. 10, but still at $f_e$ from the cornea), not all the illuminated area on the retina 6 is projected on the facet 20f. Therefore, the size of the footprint of rays 43 on retina 6 may be adjusted by moving prism 42 closer to the lens 7', that modifies slightly the divergence of rays 43 behind lens 7' and increases the size of the illuminated footprint on the retina 6. The tilt of rays depends on the off axis position of prism 42, out of point 72. Similarly, due to the off axis placement of prism 52, area of facet 20f illuminated by reference rays 53 is shifted off-axis. This off-axis shift however matches the placement of the off-axis projected image out of sample 6, of the area covered by rays 81 corresponding to the off-axis illuminated area on retina 6.

Fiber 5 and prism 72 may be shifted closer to lens 8 to create a slight divergent beam of rays 53. The off axis launch of the beam 41 secures none to little reflection from the eye lens 7'.

Figure 11:
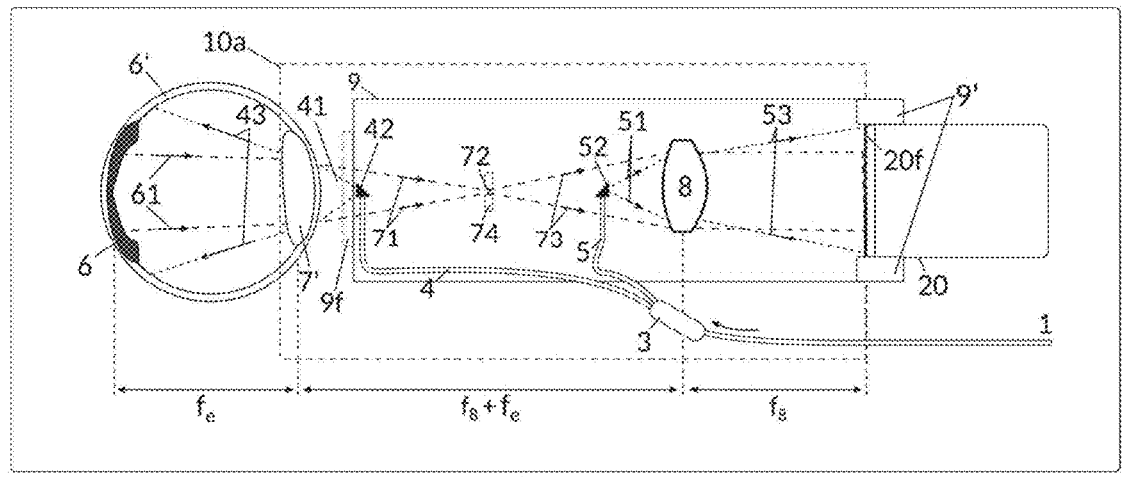
FIG. 11 shows another embodiment of the adapter to image the retina in an eye.

To enlarge the area of the retina 6 illuminated even more, fiber 4 can be shifted closer to eye lens 7', as shown in the embodiment of the adapter 10a, in FIG. 11. In this case, to reproduce the reference wave curvature in terms of optical path difference, prism 52 is also placed closer to lens 8.

The enclosure 9 is open towards the eye, containing the lens 8, prisms 42 and 52, aperture 74 and the fiber splitter, 3, placed outside (FIG. 2) or just inside (FIG. 2'). Optionally, a protecting window 9f may be used, shown in dashed line in both embodiments in FIGS. 10 and 11.

Figure 12A:
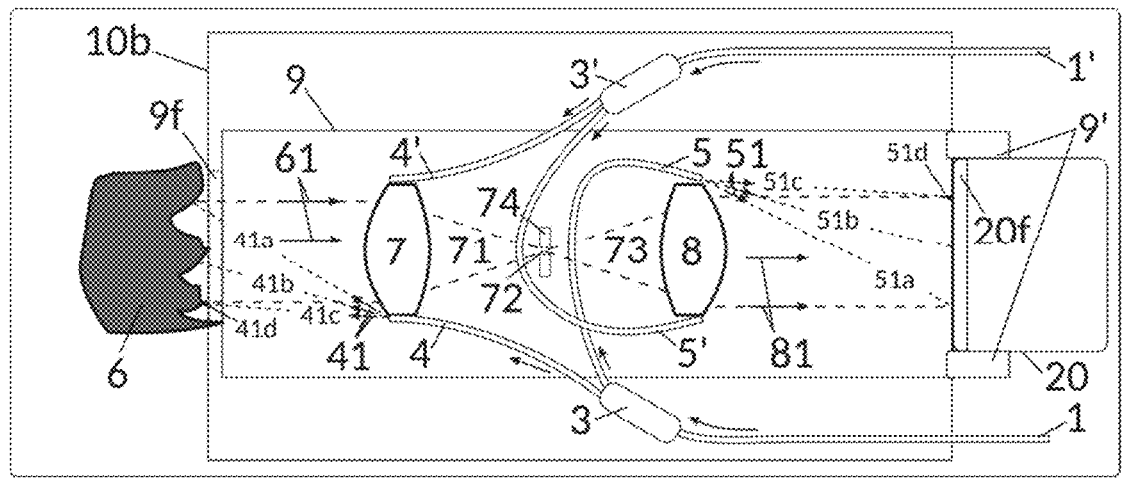
FIG. 12A shows, in diagrammatic form, the main elements of an adapter that receives light via two fibers, where sets of rays from the splitter 3 are shown only.
Figure 12B:
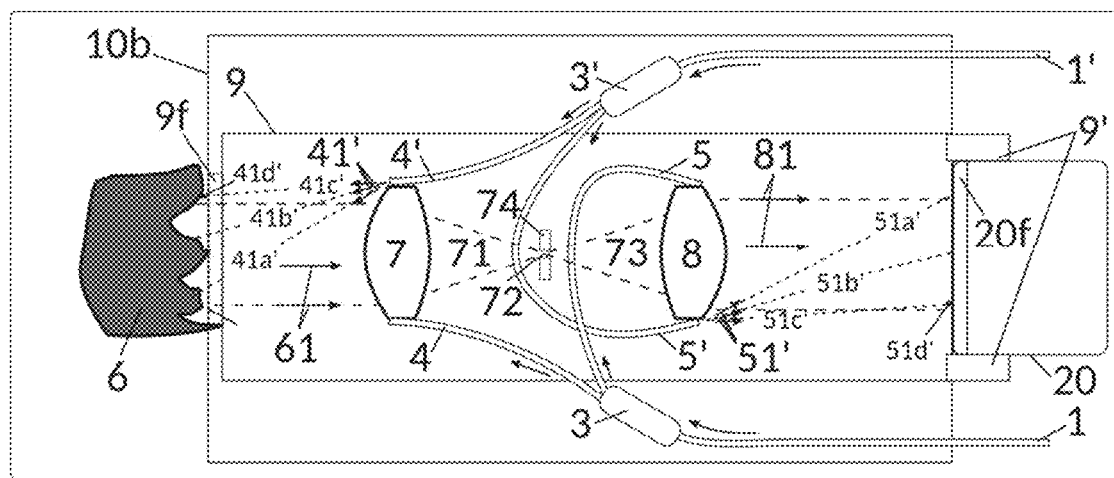
FIG. 12B shows, in diagrammatic form, the main elements of an adapter that receives light via two fibers, where sets of rays from splitter 3' are shown only.

FIGS. 12A and 12B show an improved embodiment of the adapter, as 10b, where there are two feeding fibers, 1 and 1', feeding the adapter 10b, each fiber feeding its own interferometer. For clarity, rays in the two interferometers are shown separately in FIGS. 12A and 12B of the same embodiment 10b. Feeding fiber 1' drives a second splitter 3' that launches light into two fibers, sample fiber 4' and reference fiber 5'. An immediate utility of such an embodiment is improving the light collection in respect to polarization. As shown in FIG. 2, 2', 2", there is an angle 82 between the normal to the facet 20f, i.e. along the direction of sample rays 81, mainly on axis that make a variable angle with the reference rays 51a, 51b and 51c, with the maximum angle for ray 51a. In FIG. 3, even the sample rays exhibit different angles, depending on the place of origin in the sample 6. This has an immediate effect on the polarization. If the polarization of the light in rays 81a, b, c is perpendicular to the figure, there should not be any variation in the interference contrast. However, if the polarization orientation is in the figure plane, a decrease of interference visibility is expected, most accentuated for ray 51a than for ray 51c in FIG. 2, 2' and 2", due to a larger angle between the polarization directions of the two interfering waves.

In FIG. 3, if the polarization orientation is in the figure plane, a decrease of interference visibility is expected, most accentuated for ray 51c than for ray 51a due to a larger angle between the polarization directions of the two interfering waves.

A possible variation of the embodiment 10b in this respect is where the splitters 3 and 3' are polarization maintaining, adjusted in their fiber orientation to launch light into the adapter 10b, via rays 41 and 51, respectively 41' and 51', whose polarization may be adjusted perpendicular to that of the figure plane.

Another variation of the embodiment 10b is where the two polarization maintaining splitters, 3 and 3', launch orthogonal polarizations to the sample 6 in case polarization sensitive OCT is needed, such as in case of identifying collagenous links in the sample investigated 6. It should be understood that further analyzers or waveplates can be added prior to the facet 20f for this purpose. For such an application, feeding fibers 1 and 1' may be chosen as polarization maintaining and fibers 4 and 4' are suitably rotated to launch orthogonal directions to the sample 6 and fibers 5 and 5' are suitably rotated to launch orthogonal directions to the facet 20f.

It is also known that scattering depends on angle, here the fiber 4 and fiber 4' make similar but opposed angles with the normal to the sample 6, and so, angle dependence information can be collected by sequentially using the two feeding fibers 1 and 1'.

A pseudo stereo view can also be uniquely employed by using the two splitters 3 and 3'.

A similar strategy can be applied to the embodiment of the adapter in FIG. 3, by using two feedings fibers, 1 and 1' and two splitters 3 and 3'.

Figure 13:
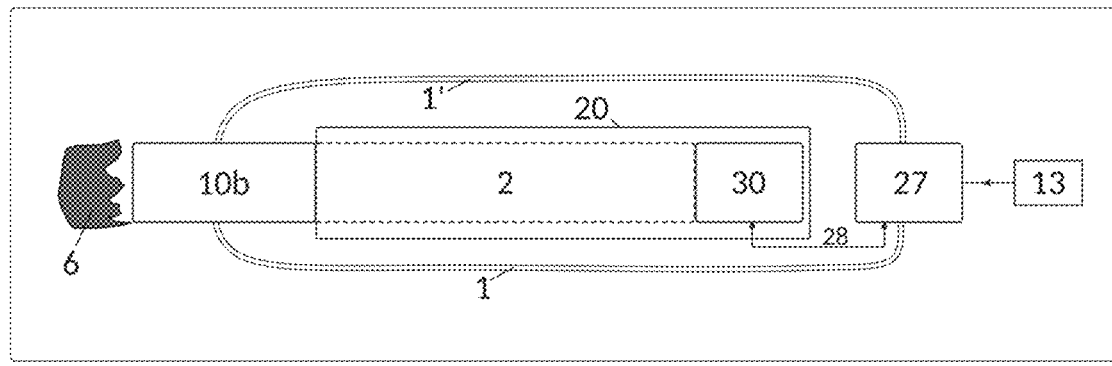
FIG. 13 discloses in a schematic diagram, an embodiment of the system that uses the adapter embodiment in FIG. 12 to implement enhanced OCT investigation.

A schematic diagram of the remote system using the adapter 10b is disclosed in FIG. 13. The two feeding fibers 1 and 1' are sequentially illuminated with swept source light from a swept source 13 via an optical switch 27. The sequence of illumination and collection is synchronized with the camera device 30 via a trigger line 28 and the two sets of images obtained can be processed to achieve different functionality as detailed above, or simply averaged to reduce the polarization effect on the fringe contrast. The optical relay device 2 is shown in dashed, i.e. the camera device 30 may receive the rays 51 and 81 either direct or via the optical relay device 2.

When images are averaged, the embodiment of the system in FIG. 13 delivers a more tolerant OCT imaging, where variation of polarization due to the off axis angle variation of rays 51 is eliminated by average of the results obtained using feeding fiber 1 and splitter 3 in one instance and feeding fiber 1' and splitter 3' in a second instance.

Another functionality of the adapter 10b could be to use two different wavelength bands, to implement spectroscopic OCT. In this case, two swept sources, 13, are used sequentially, under control from 27, covering different bands and where the camera device 30 needs to be sensitive to both spectral windows.

Figure 14:
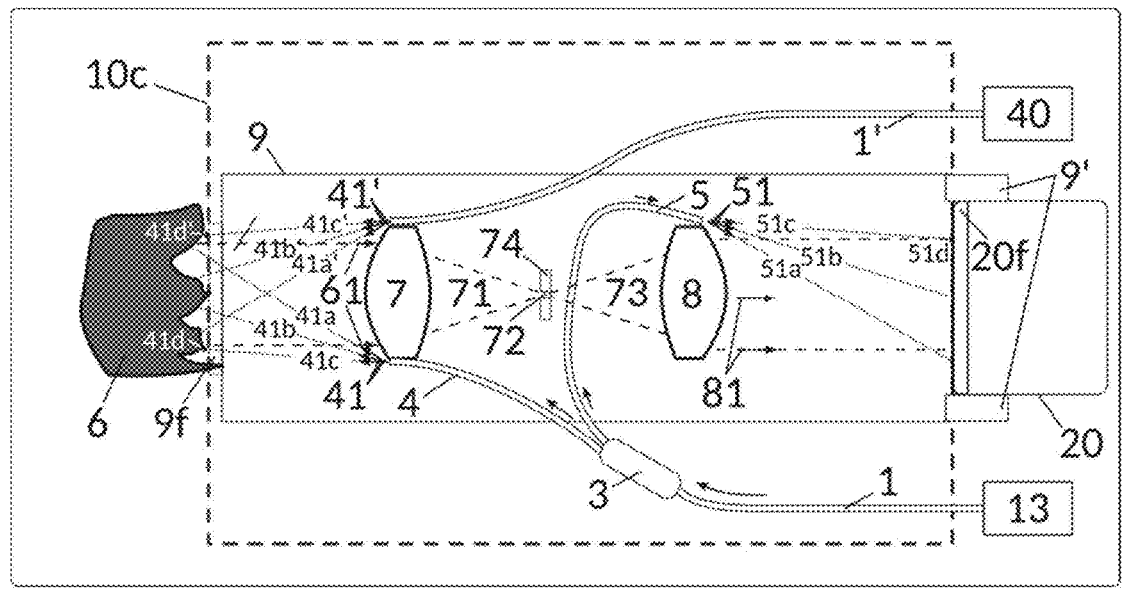
FIG. 14 discloses in a schematic diagram, another embodiment of the adapter, that is equipped with a second illuminating fiber.

Another possibility in using two feeding fibers 1 and 1' for enhanced functionality of the adapter is disclosed in FIG. 14, showing an adapter 10c. The fiber 1' is used to illuminate the sample 6 using a separate optical source 40.

Figure 15:
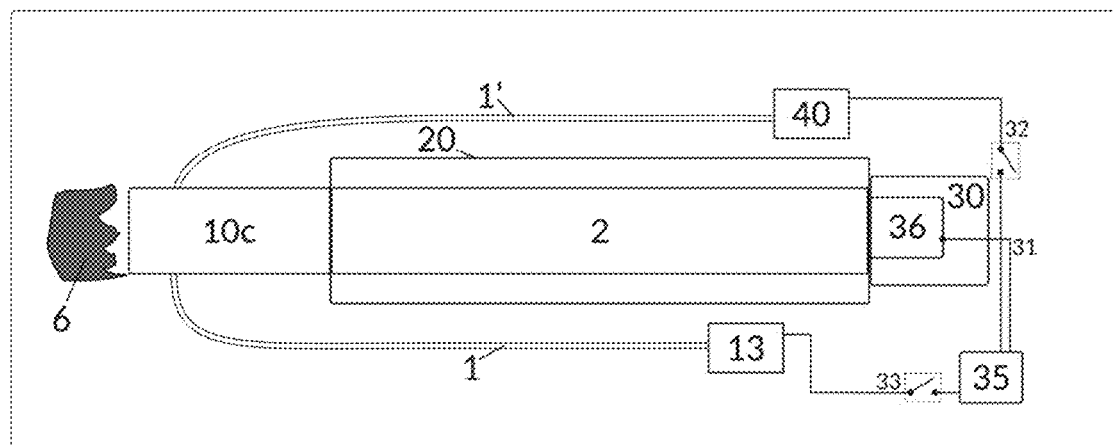
FIG. 15 discloses in a schematic diagram, another embodiment of the system, that employs the adapter disclosed in FIG. 14, to sequentially implement microendoscopy investigation in addition to OCT investigation.
Figure 15:
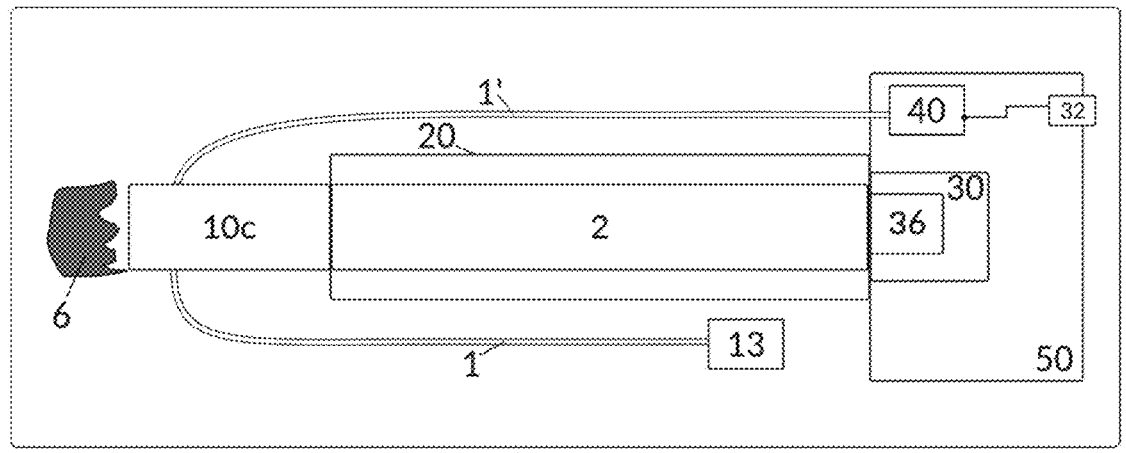

Detailed utilization of the adapter 10c is disclosed in FIG. 15. When feeding fiber 1' is used, an endomicroscopy (EM)-like image is obtained on facet 20f of the imaging device 20, delivering a global en-face image of the sample 6. In this case the feeding fiber 1' can be single mode or multimode, and the illuminating source 40, that can be monochromatic, large band, white light, in visible or infrared, or made from several such sources of different wavelengths or using a tunable optical source to enable spectroscopic imaging. When feeding fiber 1 is used, an OCT 3D volume is produced via full field (FF)-swept source (SS)-OCT, according to the method explained below. The embodiment in FIG. 15 allows pixel to pixel correspondence information between the two modalities, EM and OCT, performed sequentially, advantageous for combining expertise of clinicians using each of such modality separately, developed using EM and OCT instruments. A control block 35 triggers a camera sensor 36 used in the camera device 30 via line 31 and toggles the switch on and off of the sources 40 and 13, via respective lines 32 and 33.

Utilization of the adapter in low resource settings using a commercial digital camera or a smart phone 50, is illustrated by the embodiment in FIG. 15'. A low cost system can be implemented for cornea, skin or dental investigations. This uses the optical source 40 of the smart phone or digital camera and its own camera sensor 36, as part of the camera device 30. FIG. 15' shows the utilization of the flash as source 40 under the control of button 32 on the body of 50. In terms of frame acquisition, new smart phones are equipped with slow mode functionality that allows their camera sensors to operate at over 200 frames per second. Apple iPhones 6,7,8,X in slow modes do 220 frames per second, Sony Xperia XZ Premium does 960 frames per second. Because the sweeping requires a second, this corresponds to a low sweeping rate that allows implementation of a low cost swept source 13. This can be assembled using a semiconductor amplifier, and a low cost slow spectral tuning filter leading to a whole cost with driver as low as a few hundred $ in large quantity. There are increasing numbers of commercial grade cameras whose performance are similar to professional digital cameras in terms of pixel density and dynamic range. A main problem with commercial systems is lack of control or triggers, Here the patents U.S. Pat. Nos. 9,167,144 and 8,619,184 by A. Podoleanu are incorporated where a control signal can be provided via the smart phone flash to initiate the sweeping, phone flash being used instead of source 40 to drive fiber 1', where the flash impinges on a separate photodetector that creates an electrical signal to switch on the sweeping of the external swept source 13 (not shown).

Figure 16:
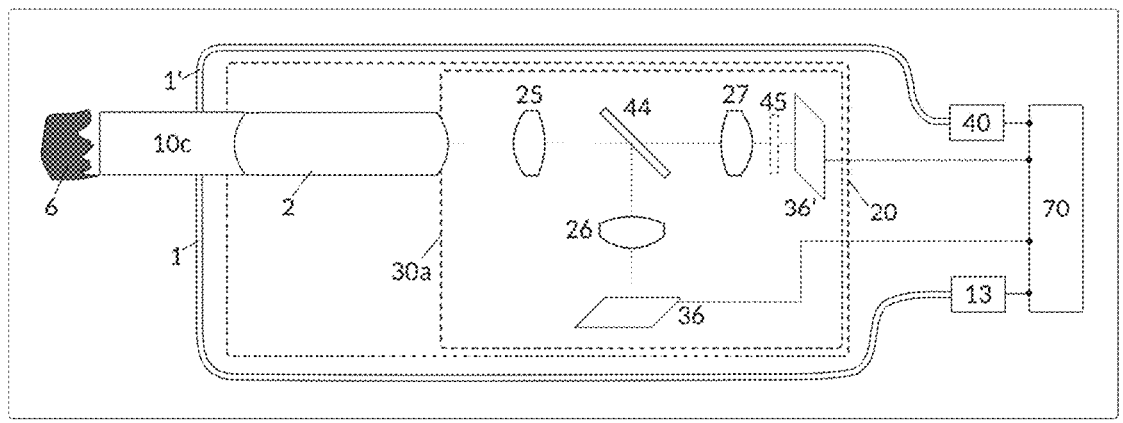
FIG. 16 discloses in a schematic diagram, another embodiment of the system, that employs the adapter disclosed in FIG. 14, to implement microendoscopy investigation in addition to OCT investigation, simultaneously.

FIG. 16 discloses an embodiment that operates simultaneously in the endomicroscopy (EM) and full field (FF) swept source (SS)-OCT regimes, employing the adapter 10c and where at the proximal end, a dichroic splitter 44 is used in the camera device 30a, that separates the light returning from sample 6, fed by feeding fiber 1 from the swept source 13, at for instance 850 nm, from that coming from a source 40 emitting in visible wavelength range. In this way, a conventional EM FF en-face image is presented together with 3D views of the sample volume obtained via FF-SS-OCT. Lenses 25 and 26 transfer the image from the proximal end of the optical relay device 2 to a 2D camera sensor 36 used for FF-SS-OCT and lenses 25 and 27 transfer the image towards a 2D camera sensor 36' for EM. For OCT examination, feeding fiber 1 may be single mode, connected to a swept source 13. For EM FF en-face imaging, a multimode fiber as feeding fiber 1' can be used.

It may also be possible that in the EM regime, the embodiment in FIG. 16 is used to deliver fluorescence images, or Raman measurements or imaging, excited by either source 40 or 13, by using an optional filter, 45, after the dichroic splitter 44, here placed after lens 27, to reduce the excitation wavelength and band pass the useful radiation, using a combination of notch and pass-band filters. If the fluorescence excitation is carried out by the same source 13 used for SS-OCT, then a single feeding fiber is sufficient to ensure FF-SS-OCT and EM FF imaging.

The camera device 30a that contains all elements 25, 44, 26, 36, 27, 45 and 36', can be assembled into a small portable device.

Methods to Produce OCT Images

Both time domain and spectral (Fourier) domain methods can be applicable to the adapter. However, time domain would require some mechanical variation of one of the paths within the adapter to produce phase modulation or path scanning. Therefore, the method of choice here is that of Fourier domain OCT, based on swept source interrogation and that of spectrometer based interrogation (spectral OCT).

Producing Full Field Swept Source OCT Images

Here, frames are acquired by the camera sensor 36 in the embodiments above, while the optical frequency of the swept source 13 is tuned. A number N of frames secures N spectral pixels that via a Fourier transform would lead to N/2 spatial axial pixels. Considering an axial resolution of 10 microns, for an axial range of 1 mm, 100 spatially resolved points along axial coordinate are needed, i.e. at least N=200 frames. Considering a bundle that can relay a square raster of 2.5 mm with a 5 microns lateral resolution, $M^2=500\times500$ pixels would be needed. This would correspond to a volume of 500×500×200 pixels out of the sample 6 volume.

Such a method is termed as full field swept source OCT, as explained in the U.S. Pat. No. 9,383,187 by A. Podoleanu and A. Bradu. Each frame in the sequence is acquired at a different optical frequency excitation. There are inexpensive fast cameras that with different regions of interest can do hundreds of Hz to kHz frame rates, such as Mikrotron EOSens and PCO. After collection of a number N of frames during a sweep time of the swept source, a sequence of N spectral pixels is produced, for each lateral pixel in the camera of the relay optic device. Each such sequence out of $M^2$ is processed to produce depth resolved information, i.e. an A-scan (reflectivity profile in depth), for each lateral pixel. Grouping all $M^2$ A-scans together, a whole volume of the sample 6 is represented. If the tuning is linear in optical frequency, then a Fourier transform applied to each such sequence returns an A-scan. If the tuning is nonlinear, then resampling of data is needed. This would add complexity and cost and time to the signal processing.

According to calculations of OPDs in Equations (1), (2), (3) and (4) applicable to FIG. 2, 2' and 2", there is an inherent dispersion of the adapter construction. For the scope of this method, U.S. Pat. No. 9,383,187 on Master Slave OCT and patent application 2017/0138721 A1, by A. Podoleanu et al on Complex Master Slave OCT are here fully incorporated. Master slave and complex master slave technologies can use data that is produced by nonlinear sweeping sources and are tolerant to dispersion in the interferometer. Such methods were applied for full field swept source OCT as reported in the paper: "Full-Field Swept Source Master-Slave Optical Coherence Tomography", by J. Wang, A, Bradu, G. Dobre and A. Podoleanu, published in the Photonics Journal, IEEE, 2015, Vol. 7, Issue: 4, Art. #: 3800114, DOI: 10.1109/JPHOT.2015.2461571. A similar procedure can be used here applied to a scientific grade camera as well as to a commercial grade camera. In addition to the dispersion in the interferometer configuration of the adapter, there is different dispersion encountered by interfering waves for each lateral pixel in the camera sensor 36 (due to elements of the interface optics in the adapter, thickness of lenses 7 and 8 in FIG. 2, 2', 2" and lens 78 in FIG. 3). Using a mirror as sample 6, for each lateral pixel of the camera sensor 36, a calibration file (mask) is stored. When the mirror is replaced by the sample to be investigated, for each lateral pixel, the (Complex) Master Slave method is applied using the mask for that lateral pixel.

Depending on the embodiment of the adapter, a deliberate mismatch of path locus of sample rays and path locus of reference rays is created that leads to a high density fringe pattern produced on the facet 20f. This corresponds to creating a carrier signal, equivalent to a shift in the 2D Fourier Transform (FT) space over the 20f surface. This can be advantageously employed to eliminate the DC terms and the mirror term (similar modulation of the channeled spectrum for the same modulus of optical path difference in the interferometer). Firstly, a 2-D FT is applied across the two transversal coordinates, and the negative and DC components are removed. The region containing the positive spatial frequency components is then shifted to be centered on the zero frequency, and a 2-D inverse Fourier transform (IFT) is applied. Finally, a fast FT or a Master slave operation over the spectral coordinates of the complex-valued data can be performed, obtaining a full-axial range image with no mirror terms. The density of the fringe pattern created over the facet 20f should be adjusted to the maximum density that can be processed by imaging device 20. Depending on the embodiment, this modulation can be adjusted by curving slightly the wavefronts in respect to each other, which are created by the fibers 4 and 5. An immediate disadvantage of using a carrier in FT space is that of halving the axial range, however with the advantage of mirror term elimination, a trade-off known in the art of off-axis full field swept source OCT. Processing first the lateral fringe modulation is known to the person skilled in the art as presented in Fechtig et al., *Opt. Lett.* 39(18) (2014), Fechtig et al., *Biomed. Opt. Express* 6(3) (2015) and earlier by Yasuno et al., *Opt. Express* 12(25) (2004).

Therefore, an optimum value exists for the angle 82. In the Fourier domain pair of the facet 20f, the angle 82 has to be sufficiently large to separate, the zero order interference from the first interference orders, while sufficiently small to allow correct sampling by the imaging device 20 (when using a fiber bundle 21, its density of fibers, or number of pixels in the camera sensor 36). The density of modulation along the facet 20f can be up to twice the period of the minimum period of fringes possible to be sampled by the imaging device 20.

OCT Fast Cross Sectioning Using Swept Source OCT

Figure 17:
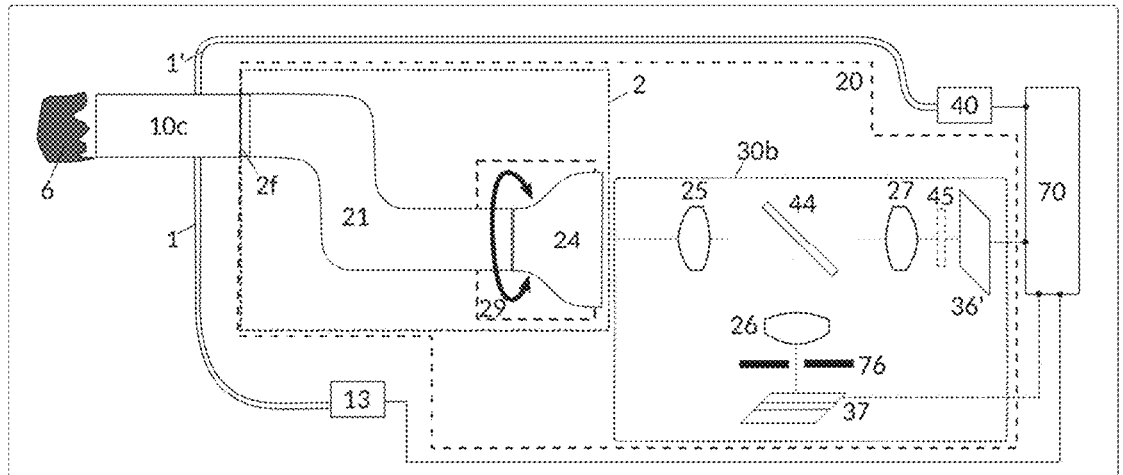
FIG. 17 discloses in diagrammatic form the main elements of an imaging instrument using the adapter in FIG. 14 to simultaneously perform B-scan SS-OCT and microendoscopy investigations.

The embodiment of the system in FIG. 17 can be used to produce fast cross section OCT images (B-scans), using a line scan camera sensor 37. This is used to select a tiny linear portion of the transferred image from facet 20f, where the camera pixel density and pixel size will determine the final lateral resolution. The lateral resolution is also influenced by one or more slits, such as 76. For better accuracy, a taper 24, may also be used, attached to the end of a flexible bundle 21 as the optical relay device. A rotation mechanism for up to 180 degrees, 29, rotates the proximal end of the flexible bundle 21, together with the optional taper 24. By rotating the fiber bundle 21 (together with taper 24) using a mechanical rotator assembly 29, cross sections through the sample 6 are obtained at different angles from the sample 6. For a sufficient large number of angles, a complete volume of the sample 6 can be obtained. The exact portion sampled by slit 76 and the camera sensor 37 is judged by inspecting the images provided by 2D camera sensor 36'. Fast B-scan imaging is obtained, where the source 13 needs to be swept to provide a spectral element within the reading time of the line scan camera sensor 37. For instance, a Basler sprint spL4096-140 km working at 250 kHz (4 microseconds per line) can be used. For a tuning band of 50 nm, at 850 nm central wavelength, axial resolution achievable is 0.44 $\lambda^2/\Delta\lambda$=6.3 microns. Considering a swept source with linewidth $\delta\lambda$=20 pm, at least 2500 spectral steps are needed. Employing 2500 spectral steps, each requiring 4 microseconds, the full scan requires 10 ms, i.e. a B-scan rate of 100 Hz. The B-scans created have the lateral size defined by the size of the line camera sensor matching the lateral size of the bundle 21 if the lenses 25 and 26 have similar focal lengths, or its magnified or demagnified size when using different focal lengths. The B-scans created have the axial range corresponding to 2500/2=1250 cycles of channeled spectrum modulation and so, the axial range is 1250×6.3 microns=7.50 mm. This is allowed by the maximum optical axial range estimated by: AR=025% $\lambda^2/\delta\lambda$=9 mm. For higher B-scan rates, fewer spectral points are acquired at the expense of a proportionately shorter axial ranges, for instance with only 125 lines for 125 frequency steps within the same tuning bandwidth, a 1 kHz B-scan rate becomes achievable covering an axial range of only 0.75 mm.

In this way, the two modalities, EM and OCT can be used to deliver information along rectangular directions, with the EM delivering an en-face (C-scan) oriented image, by camera sensor 36' while the OCT delivers cross section images (B-scan) by processing the OCT data, where the cross section OCT images are perpendicular to the en-face views, delivered by line camera sensor 37.

It may also be possible that in the EM regime, the embodiment in FIG. 17 is used to deliver fluorescence images, by using an optional filter, 45, shown in dashed line, after the dichroic splitter 44.

The camera device 30b that contains all elements 25, 44, 26, 76, 37, 27, 45, 36', can be assembled in a small portable enclosure.

In the embodiment in FIG. 17, a large area is illuminated on the sample 6 and a large area on the facet 20f, while a line is used out of both areas. This is not efficient but allows the whole volume of the sample to be explored by rotating the end of bundle 21 and taper 24 using the rotation mechanism 29. Efficiency can be improved by concentrating light into line footprints using specialized tiny elements at the end of fibers 4 and 5 in the adapter 10c. Such devices do not need to generate sharp lines, only approximate line shapes on both the sample 6 and the facet 20f of the imaging device 20, here the facet of the bundle 21, because the transversal resolution is dictated by the size of pixels on the line scan camera sensor 37 and the width of slit 76. Given the miniature elements, these lines are thick or distorted, but they do not determine the transversal resolution.

The approximate lines are merely used as to make the illumination and collection more efficient when B-scan OCT cross sections are produced. Such devices can be GRIN cylindrical lenses known in the art to focus light from laser diode chips.

Figure 18A:
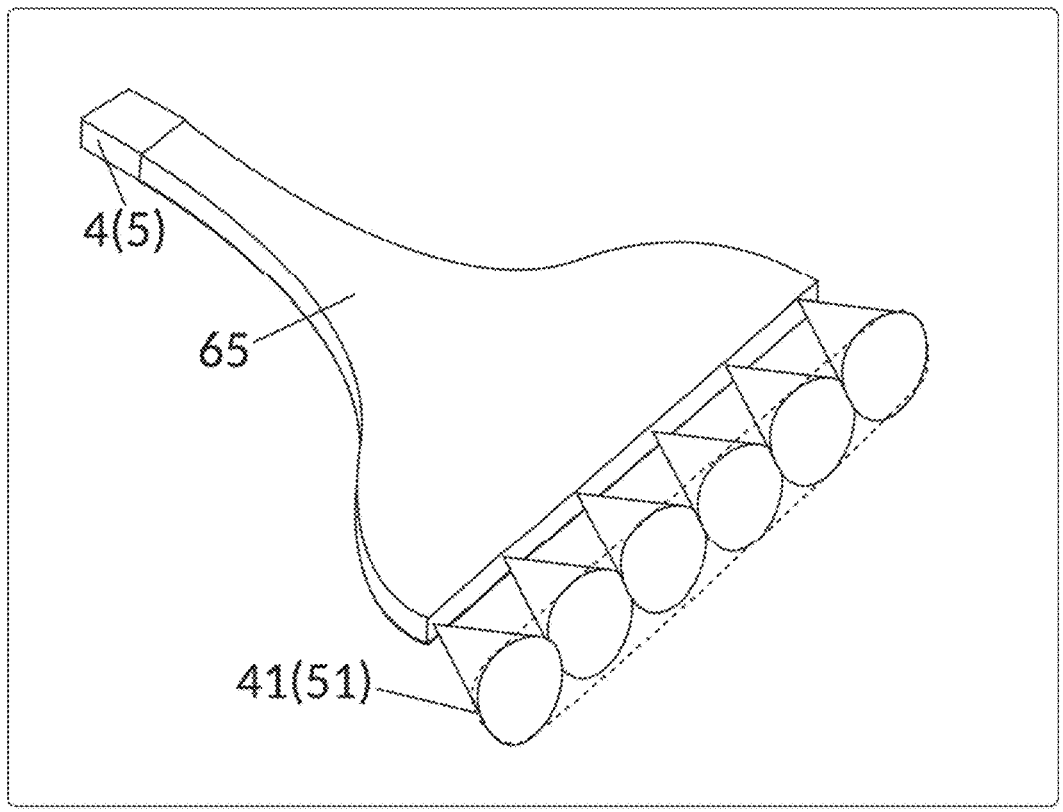
FIG. 18A shows a linear taper to be used on ends of fibers to create line illumination.
Figure 18B:
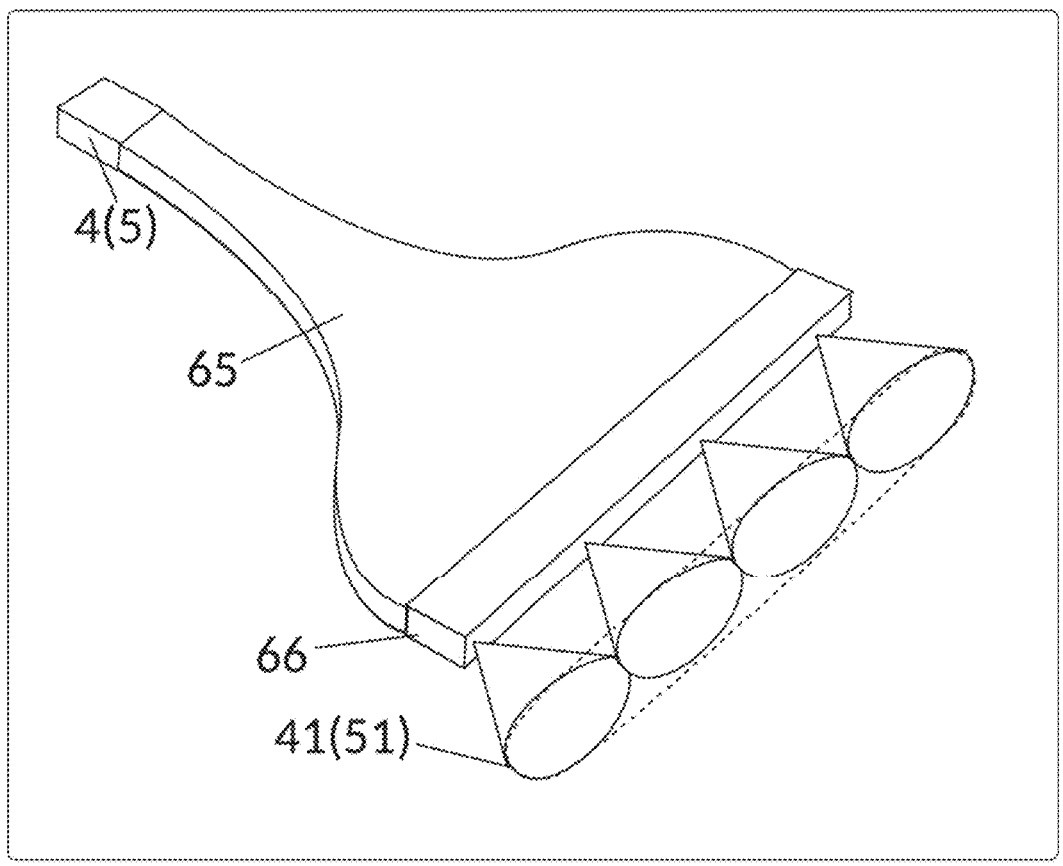
FIG. 18B shows a linear taper terminated by a cylindrical GRIN lens, used to constrict the divergence of the beam along the direction perpendicular to the taper.

Other such devices that can project lines directly from single mode fiber are disclosed in FIGS. 18A and 18B. FIG. 18A shows a line fiber taper, 65, this can be used at the end of one of the fiber 4 or 5 or on both. FIG. 18B shows a group of elements, a line taper 65 and a GRIN cylindrical lens, 66.

Figure 19:
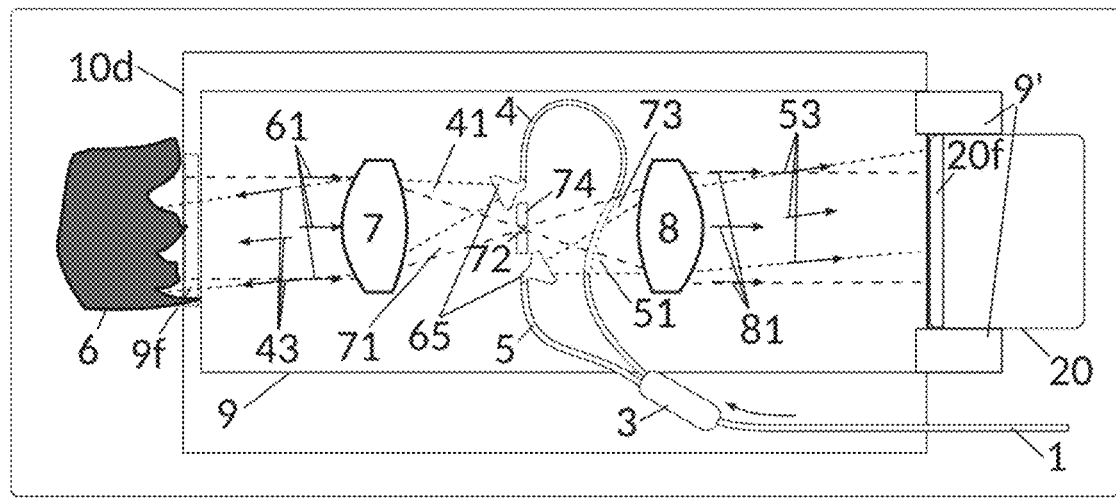
FIG. 19 discloses, in diagrammatic form, an embodiment of the adapter where lines are projected on the sample and on the optical relay device.

An adapter, 10d, using line fiber tapers 65 is disclosed in FIG. 19. Here the line fiber tapers 65 are placed close to point 72, but sufficiently away not to obscure the imaging. The fiber tapers 65 are oriented perpendicularly to the drawing plane. Via lenses 7 and 8, the lines projected on the sample 6 and facet 20f respectively are rotated into the sketch plane.

Figure 20:
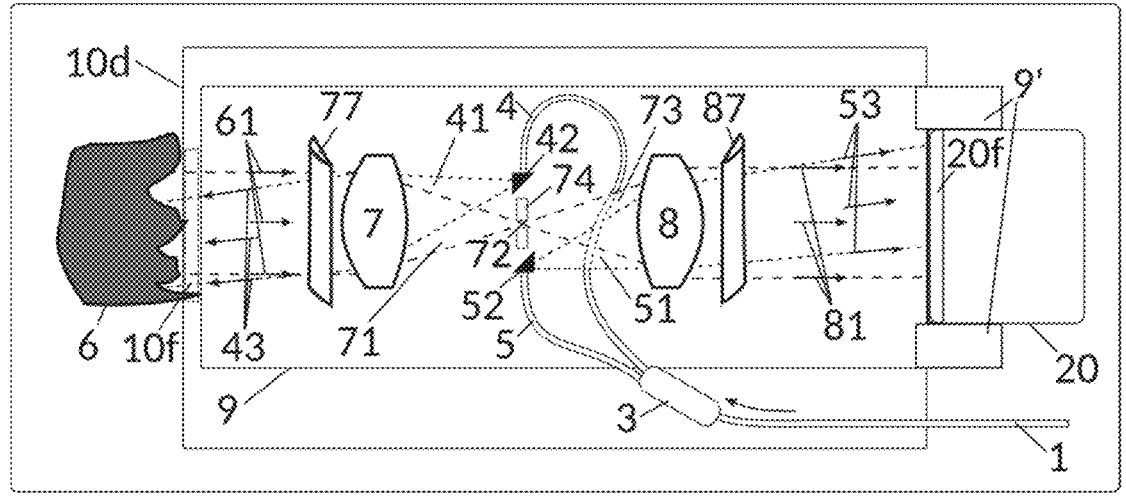
FIG. 20 discloses, in diagrammatic form, another embodiment of the adapter where lines are created on the sample and on the optical relay device.

FIG. 20 discloses another embodiment of the adapter, 10d. Here, close to lenses 7 and 8, cylindrical lenses 77 and 87 are placed. In this way, a telescope is created to transfer a line from sample 6 to a line on facet 20f. The lines are contained in the sketch plane.

OCT Fast Cross Sectioning Using Spectrometer Based OCT

Figure 21:
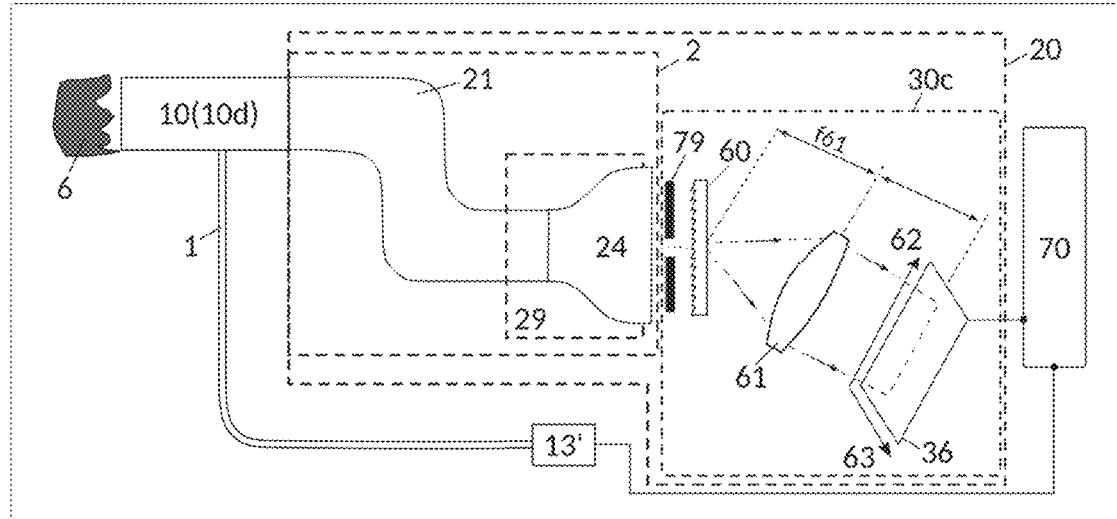
FIG. 21 discloses in diagrammatic form the main elements of an imaging instrument using the adapter in FIG. 19 or FIG. 20 to perform B-scan spectrometer-based OCT.

The embodiment in FIG. 21 uses the adapter 10 or 10d and a broadband optical source 13' such as a superluminiscent diode. A slit 79 selects a line of pixels from the optical relay device, 2. Using a diffraction grating in transmission, 60, spectral decomposition of the spectrum of interfered light is produced. In the embodiment in FIG. 21, the diffraction takes place in the plane of the figure. The slit 79 is elongated along a direction perpendicular on the figure plane. The lens 61 placed at its focal length away from 60 leads to an image in the plane of the camera sensor 36, along the spectral direction 62 determined by diffraction and along the lateral direction 63, parallel to the direction of slit 79. Data is processed by PC 70. Again, for processing of signal in the rows of the camera sensor 36 along spectral direction 62, either an FFT or (Complex) Master Slave method can be used. For the reasons mentioned above, i.e. dispersion in the interferometer and nonlinearity in the spectrometer, (Complex) Master Slave method may be utilized as explained in the U.S. Pat. No. 9,383,187 and patent application 2017/0138721 A1.

The optical relay device 2 is terminated onto the camera device 30c that contains all elements 79, 60, 61, 36, that can be assembled in a small portable device.

Similarly, cylindrical lenses 77 and 87 as employed in the embodiment of the adapter 10d in FIG. 20, can also be added to the previous embodiments, 10, in FIG. 2, 2', 2", 3, 6, 7, 8, 9, to the embodiment 10a in FIG. 10, 11 and to the embodiment 10b in FIG. 12 to be used to create cross section (B-scan) OCT images using either a swept source 13 as explained above in relation to the embodiment in FIG. 17 and FIG. 20 or using a broadband source 13' as explained above in relation to the embodiment in FIG. 21.

Figure 22:
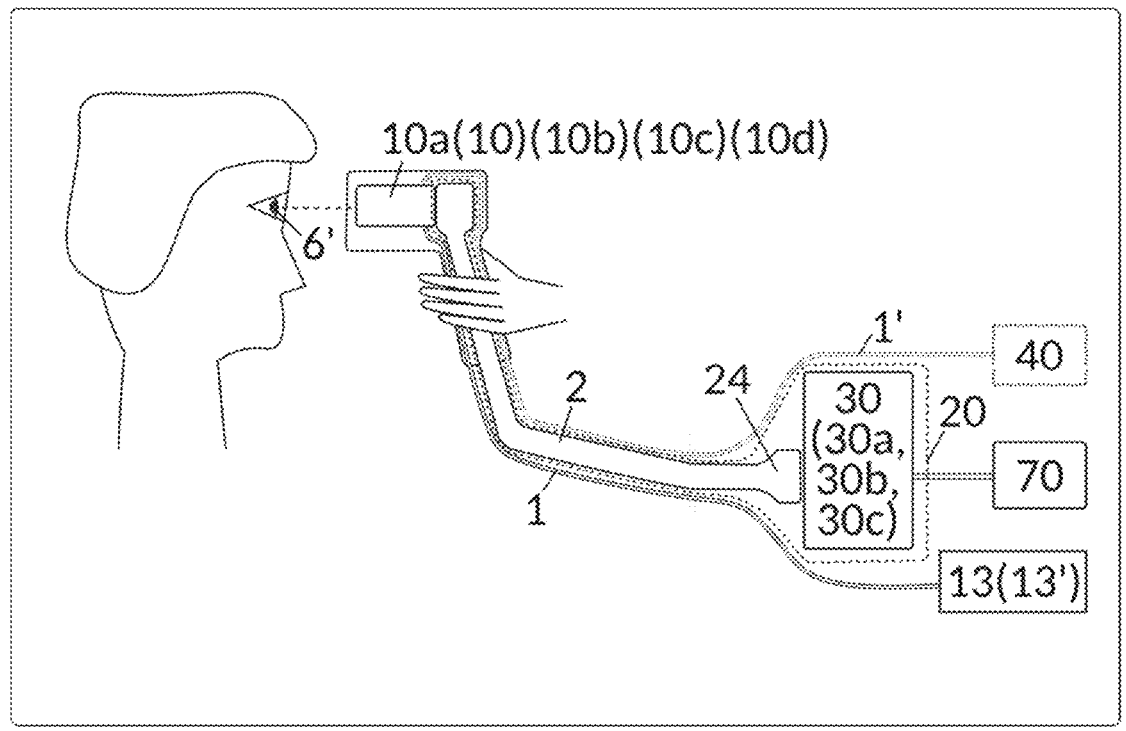
FIG. 22 discloses, in diagrammatic form, a system equipped with a hand held probe containing the adapter.

FIG. 22 shows in diagrammatic form, a portable system using the adapter. An adapter 10a with single mode fiber 1 placed in front of a bundle 21 can be made into a lightweight hand-held probe to image the eye. This contains low weight optical components, no scanning devices and can be very light and placed easily in line with the eye, or above in case the patient is in a supine position. Similarly, in the same spirit, the hand-held device can be used in dermatology or inside the mouth, for dentistry, or with proper extensions of the adapter 10 (10a, 10b, 10c, 10d) and bundle 21 to reach the esophagus, or making thin adapters, to be used for inspection into the ear, or in rigid thin forms using GRIN rod lenses 22 or telescopes or arrangements such as used in a Hopkins rod, 23, through the vitreous to serve retina vitreous surgeons.

In dashed lines, when adapters 10b and 10c are used, fiber 1' is added and source 40 is used as explained in previous figures.

The adapter can be miniaturized and used as a tethered capsule to be launched into the GI tract and collect images from inside, being totally passive.

Figure 23:
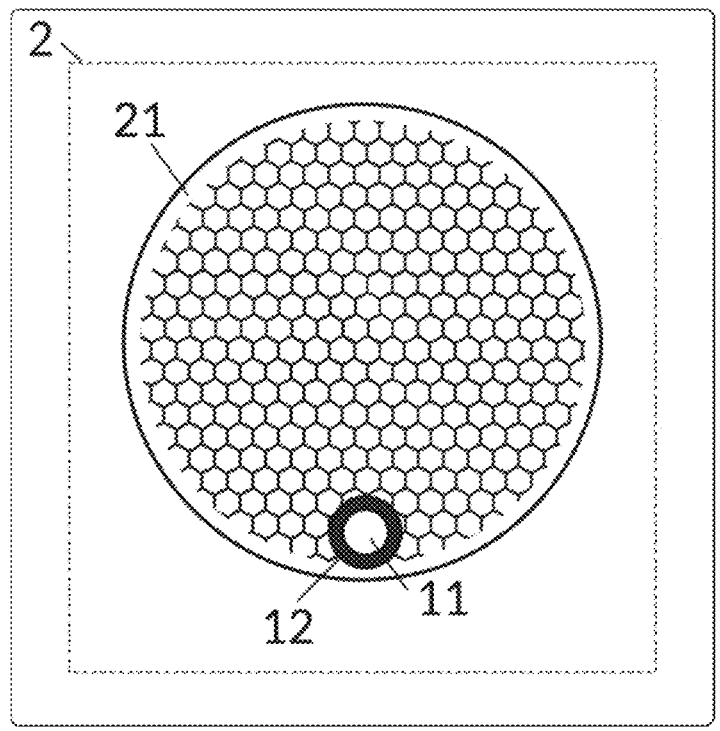
FIG. 23 shows a section through the optical relay device implemented as a bundle, where the feeding fiber is part of the bundle assembly.
Figure 23:
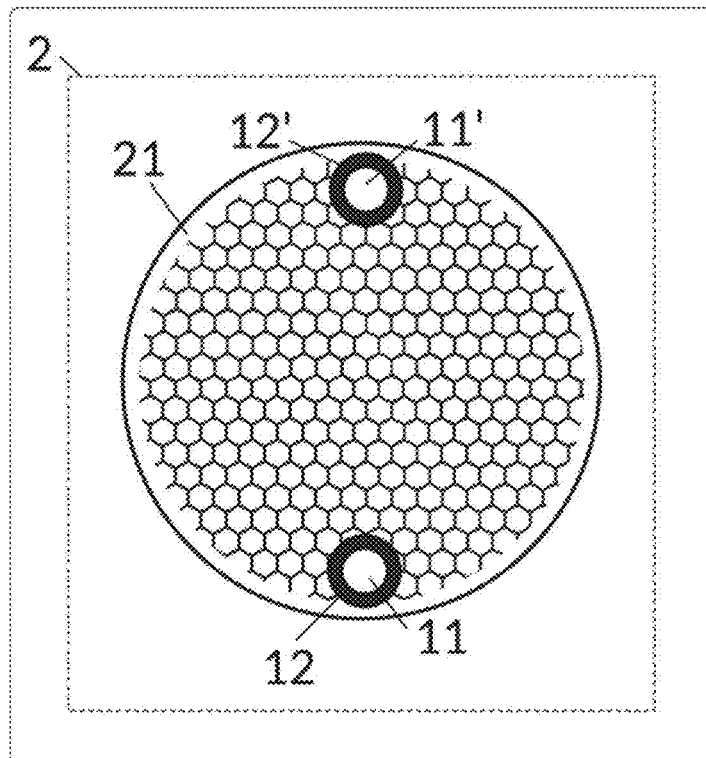
Figure 23:
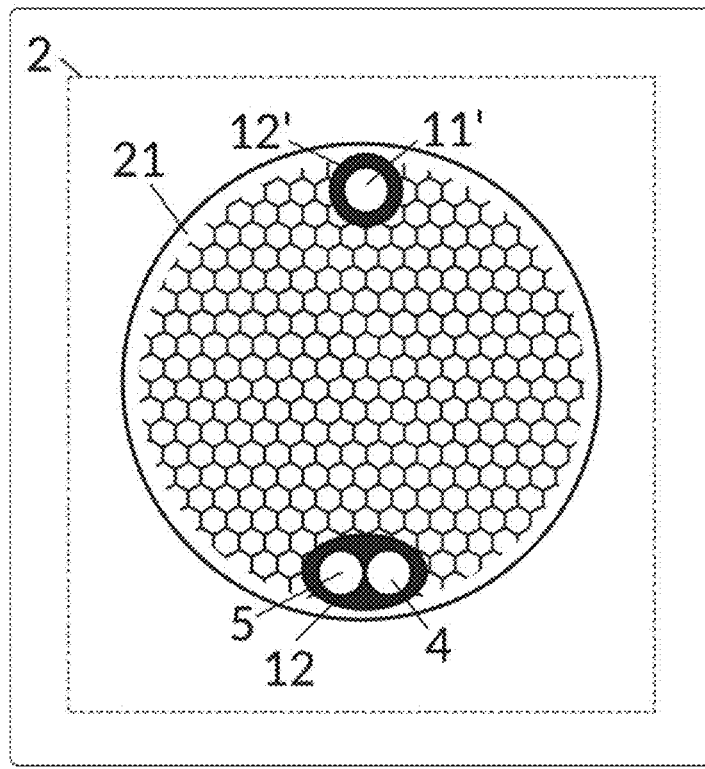

FIG. 23 shows an embodiment where the feeding fiber bringing light to the adapter 10 is part of a bundle 21, fiber 11. The fiber 11 can be a single mode fiber, with its own cladding, well separated from the rest of the fibers in the bundle 21, via a sheath 12, to avoid leaking of light inside the rest of the bundle. Fiber 11 can however be one of the other fibers in the bundle if the facet 20f collecting light from rays 51 and 81 is restricted to a smaller area of the bundle 21, away from fiber 11, according to technology known in the art. In case fiber 11 is single mode, this continues as fiber 1 to the splitter 3. In case a fiber of the bundle is used, then a single mode fiber 1 should be coupled to the fiber 11, by simple touch or fused according to means known in the art.

FIG. 23' shows a section through the optical relay device implemented as a bundle, where the two feeding fibers, 1 and 1', are supplied by fibers 11 and 11' part of the bundle assembly, separated from the rest by sheathes 12 and 12' respectively.

FIG. 23" shows a section through the optical relay device implemented as a bundle, where the two fibers part of the interferometer, 4 and 5 are run along and within the bundle, well shielded from the rest of the bundle fibers by a thin sheath 12.

By way of example, to illustrate the operation of an adapter, a system as such in FIG. 1A was assembled using an adapter as such shown in FIG. 2. A swept source, 13, with a tuning range between 820 and 870 nm, such as from Superlum, Broadsweeper, was used, scanned in 1 s over 50 nm. This spectrum width determines an axial resolution of $\delta z=2\ln 2\lambda^2/(\pi\delta\lambda)=7.8$ microns. Considering the definition of the linewidth emitted as 0.1 nm, an axial range of $\Delta z=0.25 \lambda^2/\delta\lambda=1.764$ mm results. A leached imaging bundle, as 21 was used, from Schott of ~17,000 fibers of core size of 8.4 µm, and its proximal end was imaged by a high-speed CCD 2-D camera, as camera sensor 36, (Mikrotron EOSens CL 1362) running at 400 fps with an exposure time of 100 µs, using a region of interest of 300×300 pixels. In 1 s, a total of 400 frames are acquired, each corresponding to a different optical frequency.

Figure 24:
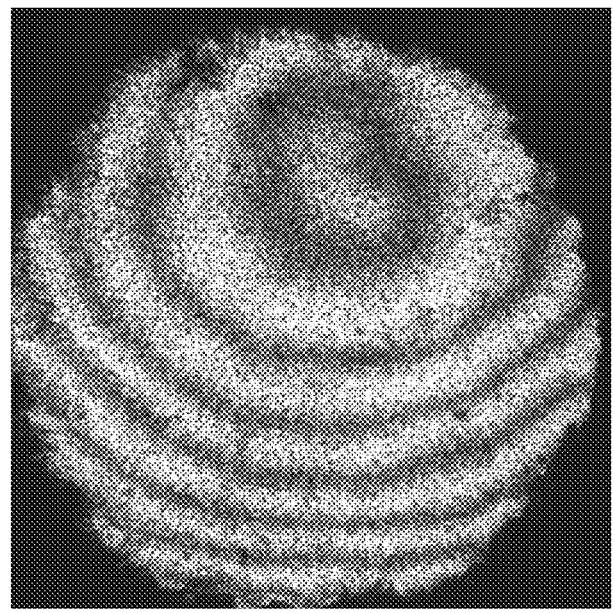
FIG. 24 presents an interference pattern using a first implementation of the system.

FIG. 24 depicts an interference pattern observed at the proximal end of the imaging bundle, while maintaining the wavelength emitted by the swept source fixed at 840 nm. The pattern was obtained by imaging a mirror as sample 6. The pattern is skewed towards the top of the image due to the fact that the mirror is not oriented perpendicularly in relation to the adapter, therefore different lateral points sit at different optical path differences due to different optical path lengths within the fan of rays 41 and 51, as explained in FIG. 4. The pattern displays an irregular periodicity, similar to Newton rings. By playing with orientation of fibers 4 and 5 and their axial position, different similar patterns are obtained. The contrast is high, proving that such a miniature adapter can deliver good interference patterns. If the mirror was curved, bulged to the outside, then the pattern would deform to become of straight parallel lines. This is in fact what happens if the mirror is replaced with tissue, where a regular structure of fringes in the shape of parallel lines would correspond to a curved surface cut inside the sample 6 as determined by the curvature of the reference wavefront due to the tilt and position of fiber 5. This is not a problem for the operation of the adapter, only that the user should be aware.

Figure 25:
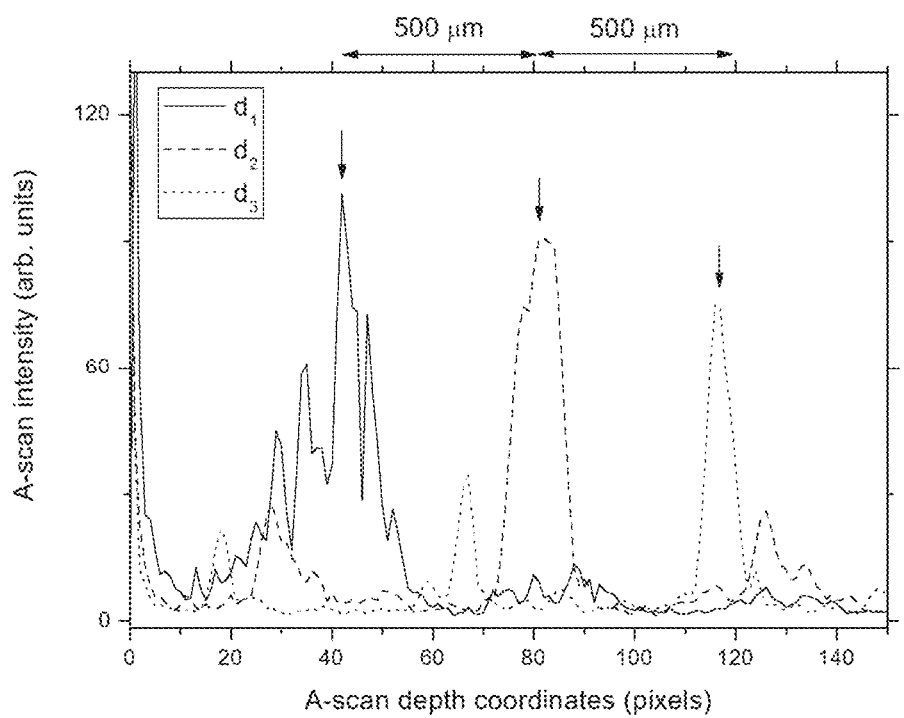
FIG. 25 shows A-scans obtained with a first implementation of the system.

Then the swept source was switched to sweeping. Signal from a pixel in the center of the camera sensor 36 was selected. Using N=400 spectral values (for the 400 frames acquired), a signal in time is generated that correspond to the channeled spectrum at the interferometer output. Then a Fourier transform of such signal determines an A-scan profile, as shown in FIG. 25. For three optical path differences, $d_1,d_2,d_3$, spaced by 500 µm between them, three A-scans are shown. The optical path difference can be changed by either moving the mirror away from the adapter or by modifying the reference length. Here we modified the air path in the reference path length, as moving the mirror would not correspond to a real situation where rays are reflected from the surface of the sample, but using rays from inside the sample along the adapter axis. Such A-scans can be produced for each pixel of the camera. The A-scans correspond to a 10 pixel-thick column of 400 data within the OCT volume stack, located transversally at a coordinate (150, 150).

Reference was primarily made to measurements and imaging using cameras, but arrays of detectors can be used instead. Lenses are shown for simplicity, but they may include groups of lenses or GRIN rods according to technologies known in the art. Fiber splitting was employed to separate the optical paths between the two arms of the interferometer, but other means are possible to achieve such separation, compatible with miniaturisation.

Full field illumination was presented almost symmetrical with respect to the enclosure of the adapter, but this can also refer to a configuration where only a fraction of the aperture is useable, if the adapter is combined with other imaging or handling tools in endoscopy.

The foregoing disclosure has been presented for the sake of illustration and description only. As such, it is not intended to be exhaustive or to limit the apparatuses and methods to the precise form disclosed.

The invention claimed is:

1. An apparatus for imaging of a sample, the apparatus comprising:
   an adapter;
   an imaging device with an input facet; and
   a first optical source,
   wherein the adapter comprises:
      an enclosure comprising interface optics configured to produce an image of the sample on the imaging device;
      a first feeding fiber, optically coupled to the first optical source;
      a first splitter, having an input optically coupled to the first feeding fiber, a first output, and a second output; and
      a first reference fiber, optically coupled to the second output of the first splitter,
   wherein the enclosure is arranged distally of the imaging device, such that, in use, it is arranged in an optical path between the sample and the imaging device,
   the enclosure having an optical axis, being an axis connecting a center of an area of the sample to be imaged and a center of the interface optics,
   wherein the first splitter is configured to send light to the sample via the first output, as an off-axis beam, so as to illuminate the sample with divergent incident light,
   wherein the first splitter is further configured to send light to the imaging device via the second output, through the first reference fiber, wherein the first reference fiber outputs reference light, so as to illuminate the imaging device with divergent reference light, and the first splitter is configured such that the reference light propagates as the off-axis beam, and
   whereby scattered light from the sample is non-collinear with the reference light at the output of the first reference fiber, and the scattered light is superposed with the reference light to produce interference on the input facet of the imaging device.

2. The apparatus according to claim 1, further comprising a first sample fiber, optically coupled to the first output of the first splitter, wherein the first splitter is configured to send incident light to the sample through the first sample fiber.

3. The apparatus according to claim 2, wherein the first splitter is spaced from the enclosure and wherein both the first sample fiber and the first reference fiber are arranged along at least a part of the imaging device.

4. The apparatus according to claim 2, wherein a fiber end of the first sample fiber and a fiber end of the first reference fiber are equipped with diverging elements to increase a divergence of light coming out from the respective fiber ends.

5. The apparatus according to claim 1, wherein the first splitter is arranged either inside or adjacent to the enclosure and wherein the first feeding fiber is arranged along at least a part of the imaging device.

6. The apparatus according to claim 1, wherein:
   the first feeding fiber forms the first output of the first splitter; and the first splitter is configured to provide light for the second output by reflection at a tip of the first feeding fiber.

7. The apparatus according to claim 1, wherein the sample is illuminated with the divergent incident light from one side of the optical axis and the imaging device is illuminated with the divergent reference light from a symmetrically opposite side of the optical axis.

8. The apparatus according to claim 1, wherein the interface optics comprise or consist of one or more lenses.

9. The apparatus according to claim 8, wherein at least one of the one or more lenses is a GRIN rod lens.

10. The apparatus according to claim 8, where all of the one or more lenses are a GRIN rod lens.

11. The apparatus according to claim 1, wherein the imaging device comprises at least a camera device having at least a first camera sensor configured to perform optical coherence tomography in conjunction with the first optical source.

12. The apparatus according to claim 11, wherein the imaging device further comprises an optical relay device arranged in an optical path between the enclosure and the camera device.

13. The apparatus according to claim 12, further comprising a fiber bundle comprising a plurality of optical fibers, wherein the optical relay device comprises at least some of the optical fibers of the fiber bundle, and wherein the first feeding fiber is part of the plurality of optical fibers in the fiber bundle.

14. The apparatus according to claim 11, wherein the optical relay device comprises or consists of one of or any combination of two or more of: a GRIN rod; a telescope; a Hopkins rod; and a fiber taper.

15. The apparatus according to claim 11, wherein the camera device further comprises a dichroic splitter and a second camera sensor device, wherein the dichroic splitter has a first output optically coupled to the first camera sensor and a second output optically coupled to the second camera sensor device, and wherein the first optical source is configured to excite fluorescence or a Raman signal which the second camera sensor device is configured to sense.

16. The apparatus according to claim 1, further comprising:
    a second optical source; and
    a second feeding fiber optically coupled to the second optical source, to bring light to the enclosure.

17. A method of imaging of a sample, the method comprising:
    using a first optical source, sending light via a first feeding fiber optically coupled to the first optical source to a first splitter having an input optically coupled to the first feeding fiber, a first output, and a second output, wherein a first reference fiber is optically coupled to the second output of the first splitter;
    using the first splitter, splitting the light into a sample diverging beam and a reference diverging beam;
    directing, via the first output, the sample diverging beam towards the sample as an off-axis beam, so as to illuminate the sample with divergent incident light;
    receiving scattered light returned from the sample;
    using a reference fiber optically coupled to the first splitter via the second output, directing the reference diverging beam towards an input facet of an imaging device so as to illuminate the imaging device with divergent reference light, wherein the first splitter is configured such that the reference light propagates as the off-axis beam;
    using interface optics of an enclosure having an optical axis being an axis connecting a center of an area of the sample and a center of the interface optics, directing the scattered light towards the input facet of the imaging device to produce an image of the sample on the input facet;
    producing an interference pattern on the input facet of the imaging device as result of superposition of the scattered light and of the reference diverging beam, wherein the scattered light is non-collinear with the reference light at the output of the first reference fiber;
    using a camera device comprising at least a camera sensor device, acquiring images of the interference pattern; and
    processing the acquired images to obtain depth-resolved information from inside the volume of the sample.

18. The method according to claim 17, wherein the optical source is a swept source configured to emit a spectrum that is variable, and wherein a number N of images $I_j$ is acquired, for j=1, 2, . . . N, with each image $I_j$ being acquired under a different spectrum emitted by the swept source and wherein, for each pixel in a row of pixels of the camera sensor device, a signal s(j) is produced,
    wherein the processing to obtain the depth-resolved information is based on complex master slave interferometry that extracts complex reflectivity values A(p), for p=1, 2, . . . N/2, from the signals s(j),
    the method further comprising deriving, from the complex reflectivity values A(p), at least one of or any combination of two or more of: a one-dimensional axial reflectivity profile; a 2-D cross-sectional OCT image; a 2D enface image; and a 3-D rendered volume.

19. The method according to claim 17, wherein the optical source is a broadband source and wherein the camera sensor device is a 2D camera sensor device and the camera device further comprises a diffraction grating, wherein the 2D camera sensor device is behind the diffraction grating, thereby forming a spectrometer,
    the method further comprising projecting, using the interface optics, a line on the sample, wherein the direction of the line corresponds with a row of pixels on the 2D camera sensor device and wherein, for each given pixel in the row of pixels, a spectrum is projected over a column of pixels including the given pixel,
    wherein, for each given pixel in the row of pixels, a signal u(v) is produced from the projected spectrum and the processing to obtain the depth-resolved information is based on complex master slave interferometry that extracts complex reflectivity values A(p), for p=1,2 . . . V/2, from each u(v),
    the method further comprising combining the complex reflectivity values A(p), to produce a 2-D cross-sectional OCT image.

20. The method according to claim 17, wherein the imaging device further comprises an optical relay device in an optical path between the interface optics and the camera device, the optical relay device comprising or consisting of one of or any combination of two or more of: a fiber bundle, a GRIN rod, a Hopkins rod, a telescope, and a fiber taper.

* * * * *